(12) United States Patent
Catlett et al.

(10) Patent No.: US 9,359,630 B2
(45) Date of Patent: Jun. 7, 2016

(54) PROMOTERS FOR EXPRESSING GENES IN A FUNGAL CELL

(75) Inventors: Michael Catlett, West Sacramento, CA (US); Debbie Yaver, Davis, CA (US)

(73) Assignee: Novozymes, Inc., Davis, CA (US)

( * ) Notice: Subject to any disclaimer, the term of this patent is extended or adjusted under 35 U.S.C. 154(b) by 191 days.

(21) Appl. No.: 13/883,931

(22) PCT Filed: Nov. 30, 2011

(86) PCT No.: PCT/US2011/062663
§ 371 (c)(1),
(2), (4) Date: Jul. 11, 2013

(87) PCT Pub. No.: WO2012/075151
PCT Pub. Date: Jun. 7, 2012

(65) Prior Publication Data
US 2013/0316399 A1   Nov. 28, 2013

Related U.S. Application Data

(60) Provisional application No. 61/418,302, filed on Nov. 30, 2010.

(51) Int. Cl.
*C07H 21/04* (2006.01)
*C12P 21/06* (2006.01)
*C12N 15/80* (2006.01)

(52) U.S. Cl.
CPC .................. *C12P 21/06* (2013.01); *C12N 15/80* (2013.01)

(58) Field of Classification Search
None
See application file for complete search history.

(56) References Cited

U.S. PATENT DOCUMENTS

2004/0146975 A1   7/2004   Yaver et al.

FOREIGN PATENT DOCUMENTS

WO   2006054997 A1   5/2006

OTHER PUBLICATIONS

Bauer et al., 2010, Mycoses 53(4), 296-304.
Galagan et al., 2005, Nature 438, 1105-1115.
Lu et al., 2010, Microb Cell Fact 9, 23.
Melin et al., 2002, Mol Genet Genom 267(6), 695-702.
Pel et al., 2007—EMBL Access No. AM271028.
Pel et al., 2007, Nature Biotechnol 25, 221-231.
Richardson et al., 2007—EMBL Acces No. EY233752.

*Primary Examiner* — Michele K Joike
(74) *Attorney, Agent, or Firm* — Robert L. Starnes

(57) ABSTRACT

The present invention relates to isolated promoters and constructs, vectors, and fungal host cells comprising such promoters operably linked to polynucleotides encoding polypeptides. The present invention also relates to methods for producing such polypeptides.

20 Claims, 3 Drawing Sheets

PROMOTERS FOR EXPRESSING GENES IN A FUNGAL CELL

CROSS-REFERENCE TO RELATED APPLICATIONS

This application is a 35 U.S.C. 371 national application of PCT/US2011/062663, filed on Nov. 30, 2011, which claims priority or the benefit under 35 U.S.C. 119 of U.S. Provisional Application Ser. No. 61/418,302, filed on Nov. 30, 2010, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods for producing polypeptides. The present invention also relates to isolated promoters and to nucleic acid constructs, vectors, and host cells comprising the promoters operably linked to polynucleotides encoding the polypeptides.

2. Description of the Related Art

The recombinant production of a polypeptide in a fungal host cell, e.g., a filamentous fungal cell, may provide for a more desirable vehicle for producing the polypeptide in commercially relevant quantities.

Recombinant production of a polypeptide is accomplished by constructing an expression cassette in which the DNA coding for the polypeptide is placed under the expression control of a promoter, excised from a gene, suitable for the host cell. The expression cassette is introduced into the host cell, usually by plasmid-mediated transformation. Production of the polypeptide is then achieved by culturing the transformed host cell under inducing conditions necessary for the proper functioning of the promoter contained on the expression cassette.

The use of a fungal host cell for the recombinant production of polypeptides generally requires the availability of promoters that are suitable for controlling the expression of the polypeptides in the host cell. Consequently, there is a need in the art for new promoters for controlling the recombinant expression of genes.

Melin et al., 2002, *Mol. Genet. Genomics* 267(6): 695-702, disclose an *Aspergillus nidulans* concanamycin-induced protein C. Lu et al., 2010, *Microb. Cell Fact.* 9: 23, disclose a cipC protein in *Aspergillus niger*.

The present invention provides improved methods for producing a polypeptide in a fungal host cell.

SUMMARY OF THE INVENTION

The present invention relates to methods for producing a polypeptide, comprising: (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence having at least 60% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (ii) a promoter comprising a nucleotide sequence that hybridizes under at least medium stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof; (iii) a promoter comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (iv) a promoter comprising a subsequence of (i), (ii), or (iii) that retains promoter activity; and (via mutant, hybrid, or tandem promoter of (i), (ii), (iii), or (iv); wherein the polynucleotide encoding the polypeptide is foreign to the promoter; and (b) isolating the polypeptide from the cultivation medium.

The present invention also relates to isolated promoters selected from the group consisting of (i) a promoter comprising a nucleotide sequence having at least 60% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32, (ii) a promoter comprising a nucleotide sequence that hybridizes under at least medium stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof; (iii) a promoter comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (iv) a promoter comprising a subsequence of (i), (ii), or (iii) that retains promoter activity; and (v) a mutant, hybrid, or tandem promoter of (i), (ii), (iii), or (iv).

The present invention also relates to constructs, vectors, and fungal host cells comprising a promoter of the present invention operably linked to a polynucleotide encoding a polypeptide.

DEFINITIONS

Figure 1:
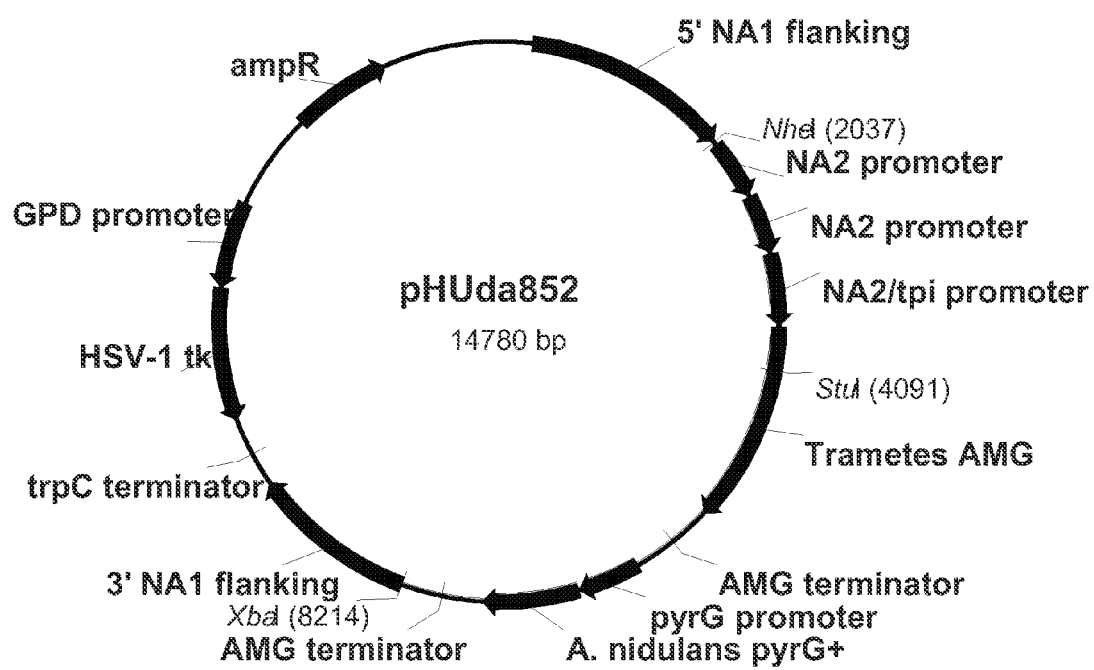
FIG. 1 shows a restriction map of pHUda852.

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding the polypeptide.

Expression: The term "expression" includes any step involved in the production of a polypeptide including, hut not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like, with a nucleic acid construct or expression vector comprising a polynucleotide of interest. The term "host cell" encompasses any progeny of a parent cell that is not identical to the parent cell due to mutations that occur during replication.

Hybrid promoter: The term "hybrid promoter" means portions of two or more (e.g., several) promoters that are linked together to generate a sequence that is a fusion of the portions of the two or more promoters, which when operably linked to a coding sequence mediates the transcription of the coding sequence into mRNA.

Isolated: The term "isolated" means a substance in a form or environment that does not occur in nature. Non-limiting examples of isolated substances include (1) any non-naturally occurring substance, (2) any substance including, but not limited to, any enzyme, variant, polynucleotide, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). A polypeptide of interest may be used in industrial applications in the form of a fermentation broth product, that is, the polypeptide is a component of a fermentation broth used as a product in industrial applications (e.g., ethanol production). The fermentation broth product will in addition to the polypeptide of interest comprise additional ingredients used in the fermentation process, such as, for example, cells (including, the host cells containing the gene encoding the polypeptide of interest which are used to produce the polypeptide), cell debris, biomass, fermentation media and/or fermentation products. The fermentation broth may be optionally subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having biological activity.

Medium stringency conditions: The term "medium stringency conditions" means for probes of at least 100 nucleotides in length, prehybridization and hybridization at 42° C. in 5×SSPE, 0.3% SDS, 200 micrograms/nil sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/nil sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic.

Operably linked: The term "operably linked" means a configuration in which a control sequence is placed at an appropriate position relative to the coding sequence of a polynucleotide such that the control sequence directs expression of the coding sequence.

Polypeptide fragment: The term "polypeptide fragment" means a polypeptide having one or more (e.g., several) amino acids absent from the amino and/or carboxyl terminus of a mature polypeptide; wherein the fragment has biological activity. In one aspect, the fragment has at least 85%, e.g., at least 90% or at least 95% of the number of amino acids as the mature polypeptide.

Polypeptide variant: The term "polypeptide variant" means a polypeptide having biological activity comprising an alteration, i.e., a substitution, insertion, and/or deletion, at one or more (e.g., several) positions. A substitution means replacement of the amino acid occupying a position with a different amino acid; a deletion means removal of the amino acid occupying a position: and an insertion means adding an amino acid adjacent to and immediately following the amino acid occupying a position.

Promoter: The term "promoter" means a DNA sequence that binds RNA polymerase and directs the polymerase to the correct downstream transcriptional start site of a polynucleotide encoding a polypeptide to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

Promoter variant: The term "promoter variant" means a promoter comprising an alteration, i.e., a substitution, insertion, and/or deletion, at one or more (e.g., several) positions. A substitution means replacement of the nucleotide occupying a position with a different nucleotide; a deletion means removal of the nucleotide occupying a position; and an insertion means adding a nucleotide adjacent to and immediately following the nucleotide occupying a position. The term "promoter variant" will also encompass natural variants and in vitro generated variants obtained using methods well known in the art such as classical mutagenesis, site-directed mutagenesis, and DNA shuffling.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0, or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice at al., 2000, supra), preferably version 3.0.0, 5.0.0, or later. The parameters used are gap open penalty of 10, gap extension penalty of 0.5, and the EDNAFULL (EMBOSS version of NCBI NUC4.4) substitution matrix. The output of Needle labeled "longest identity" (obtained using the nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence wherein the subsequence encodes a fragment having biological activity, or absent from the 5' and/or 3' end of a promoter sequence wherein the promoter subsequence has promoter activity. In one aspect, the subsequence has at least 85%, e.g., at least 90% or at least 95% of the number of nucleotides as the mature polypeptide coding sequence. In another aspect, the promoter subsequence has at least 85%, e.g., at least 90% or at least 95% of the number of nucleotides as the promoter sequence.

Tandem promoter: The term "tandem promoter" means two or more e.g., several)) promoters linked in tandem, each of which is operably linked to a coding sequence and mediates the transcription of the coding sequence into mRNA.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

The present invention relates to methods for producing a polypeptide, comprising: (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence having at least 60% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32, (ii) a promoter comprising a nucleotide sequence that hybridizes under at least medium stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof; (iii) a promoter comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (iv) a promoter comprising a subsequence of (i), (ii), or (iii) that retains promoter activity; and (v) mutant, hybrid, or tandem promoter of (i), (ii), (iii), or (iv); wherein the polynucleotide encoding the polypeptide is foreign to the promoter; and (b) isolating the polypeptide from the cultivation medium.

In the production methods of the present invention, the cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of an enzyme. Procedures for determining enzyme activity are known in the art for many enzymes (see, for example, D. Schomburg and M. Salzmann (eds.), *Enzyme Handbook*, Springer-Verlag, New York, 1990).

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Promoters

The present invention also relates to isolated promoters selected from the group consisting of (i) a promoter comprising a nucleotide sequence having at least 60% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32, (ii) a promoter comprising a nucleotide sequence that hybridizes under at least medium stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof; (iii) a promoter comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (iv) a promoter comprising a subsequence of (i), (ii), or (iii) that retains promoter activity; and (v) a mutant, hybrid, or tandem promoter of (i), (ii), (iii), or (iv); and to constructs, vectors, and fungal host cells comprising the promoter operably linked to a polynucleotide encoding a polypeptide.

In one aspect, the isolated promoters have a sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have promoter activity.

In one embodiment, a promoter of the present invention comprises or consists of the nucleotide sequence of SEQ ID NO: 1 or an allelic variant thereof; or is a subsequence thereof having promoter activity. In another aspect, the promoter comprises or consists of the nucleotide sequence of SEQ ID NO: 1.

In another embodiment, a promoter of the present invention comprises or consists of the nucleotide sequence of SEQ ID NO: 2 or an allelic variant thereof; or is a subsequence thereof having promoter activity. In another aspect, the promoter comprises or consists of the nucleotide sequence of SEQ ID NO: 2.

In another embodiment, a promoter of the present invention comprises or consists of the nucleotide sequence of SEQ ID NO: 3 or an allelic variant thereof; or is a subsequence thereof having promoter activity. In another aspect, the promoter comprises or consists of the nucleotide sequence of SEQ ID NO: 3.

In another embodiment, a promoter of the present invention comprises or consists of the nucleotide sequence of SEQ ID NO: 4 or an allelic variant thereof; or is a subsequence thereof having promoter activity. In another aspect, the promoter comprises or consists of the nucleotide sequence of SEQ ID NO: 4.

In another embodiment, a promoter of the present invention comprises or consists of the nucleotide sequence of SEQ ID NO: 5 or an allelic variant thereof; or is a subsequence thereof having promoter activity. In another aspect, the promoter comprises or consists of the nucleotide sequence of SEQ ID NO: 5.

In another embodiment, a promoter of the present invention comprises or consists of the nucleotide sequence of SEQ ID NO: 6 or an allelic variant thereof; or is a subsequence thereof having promoter activity. In another aspect, the promoter comprises or consists of the nucleotide sequence of SEQ ID NO: 6.

In another embodiment, a promoter of the present invention comprises or consists of the nucleotide sequence of SEQ ID NO: 7 or an allelic variant thereof; or is a subsequence thereof having promoter activity. In another aspect, the promoter comprises or consists of the nucleotide sequence of SEQ ID NO: 7.

In another embodiment, a promoter of the present invention comprises or consists of the nucleotide sequence of SEQ ID NO: 8 or an allelic variant thereof; or is a subsequence thereof having promoter activity. In another aspect, the promoter comprises or consists of the nucleotide sequence of SEQ ID NO: 8.

In another embodiment, a promoter of the present invention comprises or consists of the nucleotide sequence of SEQ ID NO: 31 or an allelic variant thereof; or is a subsequence thereof having promoter activity. In another aspect, the promoter comprises or consists of the nucleotide sequence of SEQ ID NO; 31.

In another embodiment, a promoter of the present invention comprises or consists of the nucleotide sequence of SEQ ID NO: 32 or an allelic variant thereof; or is a subsequence thereof having promoter activity. In another aspect, the promoter comprises or consists of the nucleotide sequence of SEQ ID NO: 32.

A subsequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32 (i.e., a truncated promoter) comprises a truncation at the 5' end so that the sequence at the 3' end closest to the ATG codon is maintained. The subsequence can be at least 600 nucleotides, e.g., at least 700 nucleotides, at least 750 nucleotides, at least 800 nucleotides, at least 850 nucleotides, or at least 900 nucleotides, that has promoter activity.

In one aspect, the isolated promoters comprise nucleotide sequences that hybridize under very low stringency conditions, low stringency conditions, medium stringency conditions, medium-high stringency conditions, high stringency conditions, or very high stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or a subsequence thereof; or the full-length complement thereof (J. Sambrook, E. F. Fritsch, and T. Maniatis, 1989, *Molecular Cloning, A Laboratory Manual,* 2d edition, Cold Spring Harbor, N.Y.).

The polynucleotide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32, or a subsequence thereof, may be used to design nucleic acid probes to identify and clone promoter DNA from strains of different genera or species according to methods well known in the art. In particular, such probes can be used for hybridization with the genomic DNA or cDNA of the genus or species of interest, following standard Southern blotting procedures, in order to identify and isolate the corresponding promoter DNA therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding promoter DNA (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described herein and has promoter activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32, or a subsequence thereof, the carrier material is preferably used in a Southern blot.

For purposes of the present invention, hybridization indicates that the polynucleotide hybridizes to a labeled nucleic acid probe corresponding to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; the full-length complement thereof; or a subsequence thereof; under very low to very high stringency conditions. Molecules to which the nucleic acid probe hybridizes under these conditions can be detected using, for example, X-ray film.

In one embodiment, the nucleic acid probe is SEQ ID NO: 1 or a subsequence thereof. In another embodiment, the nucleic acid probe is SEQ ID NO: 1. In another embodiment, the nucleic acid probe is SEQ ID NO: 2 or a subsequence thereof. In another embodiment, the nucleic acid probe is SEQ ID NO: 2. in another embodiment, the nucleic acid probe is SEQ ID NO: 3 or a subsequence thereof. In another embodiment, the nucleic acid probe is SEQ ID NO: 3. In another embodiment, the nucleic acid probe is SEQ ID NO: 4 or a subsequence thereof. In another embodiment, the nucleic acid probe is SEQ ID NO: 4. In another embodiment, the nucleic acid probe is SEQ ID NO: 5 or a subsequence thereof. In another embodiment, the nucleic acid probe is SEQ ID NO: 5. In another embodiment, the nucleic acid probe is SEQ ID NO: 6 or a subsequence thereof. In another embodiment, the nucleic acid probe is SEQ ID NO: 6. In another embodiment, the nucleic acid probe is SEQ ID NO: 7 or a subsequence thereof. In another embodiment, the nucleic acid probe is SEQ ID NO: 7. In another embodiment, the nucleic acid probe is SEQ ID NO: 8 or a subsequence thereof. In another embodiment, the nucleic acid probe is SEQ ID NO: 8. In another embodiment, the nucleic acid probe is SEQ ID NO: 31 or a subsequence thereof. In another embodiment, the nucleic acid probe is SEQ ID NO: 31. In another embodiment, the nucleic acid probe is SEQ ID NO: 32 or a subsequence thereof. In another embodiment, the nucleic acid probe is SEQ ID NO: 32.

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Aced. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In another aspect, the isolated promoters may be mutants of a promoter comprising the polynucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or a subsequence thereof that has promoter activity. The mutant promoters comprise one or more mutations (e.g., several) of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or a subsequence thereof that has promoter activity. Each mutation is an independent substitution, deletion, and/or insertion of a nucleotide. The introduction of a substitution, deletion, and/or insertion of a nucleotide into the promoter may be accomplished using any of the methods known in the art such as classical mutagenesis, site-directed mutagenesis, or DNA shuffling. Particularly useful is a procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpn I which is specific for methylated and hemimethylated DNA to digest the parental DNA template and to select for mutation-containing synthesized DNA. Other procedures known in the art may also be used.

In another aspect, the isolated promoters may be hybrid promoters comprising a portion of a promoter of the present invention and a portion of another promoter, e.g., a leader sequence of one promoter and the transcription start site from the other promoter; or a portion of one or more (e.g., several) promoters of the present invention and a portion of one or more (e.g., several) other promoters. The other promoter may be any promoter sequence which shows transcriptional activity in the fungal host cell of choice including a mutant, truncated, and hybrid promoter, and may be obtained from genes encoding extracellular or intracellular polypeptides either homologous or heterologous to the host cell. The other promoter sequence may also be a portion of a promoter of the present invention. The other promoter sequence may also be native or foreign to the polynucleotide encoding the polypeptide and native or foreign to the cell.

In another aspect, the isolated promoters may be tandem promoters comprising one or more (e.g., several) promoters of the present invention and one or more (e.g., several) other promoters. The one or more (e.g., several) other promoters may be promoters of the present invention. The one or more (e.g., several) other promoters may be promoters such as those exemplified below. Two or more (e.g., several) promoter sequences of the tandem promoter may simultaneously promote the transcription of the polynucleotide. Alternatively, one or more (e.g., several) of the promoter sequences of the tandem promoter may promote the transcription of the polynucleotide at different stages of growth of the cell. In one embodiment, the tandem promoter comprises two promoters. In another embodiment, the tandem promoter comprises three promoters. In another embodiment, the tandem promoter comprises four promoters. In another embodiment, the tandem promoter comprises five promoters.

Examples of other promoters useful in the construction of tandem promoters or hybrid promoters with the promoters of the present invention include the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, NA2-tpi promoter (a modified promoter from an *Aspergillus* neutral alpha-amylase gene in which the untranslated leader has been replaced by an untranslated leader from an *Aspergillus* triose phosphate isomerase gene: non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase; and mutant, truncated, and hybrid promoters thereof. Other promoters are described in U.S. Pat. No. 6,011,147 and by Romanos et al., 1992, *Yeast* 8: 423-488.

In the methods of the present invention, a hybrid or tandem promoter of the present invention will be understood to be foreign to a polynucleotide encoding a polypeptide even if the wild-type promoter is native to the polynucleotide. For example, in a tandem promoter consisting of at least two promoters, one of the promoters may be the wild-type promoter of the polynucleotide encoding the polypeptide.

Polypeptides

The term "polypeptide" is defined herein as a polypeptide encoded by a coding sequence that is foreign to a promoter of the present invention.

The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses polypeptides, which comprise a combination of partial and/or complete polypeptide sequences obtained from at least two different polypeptides wherein one or more (e.g., several) may be heterologous to the fungal cell. Polypeptides further include naturally occurring allelic and engineered variations of a polypeptide.

In one aspect, the polypeptide is an antibody, antigen, antimicrobial peptide, enzyme, growth factor, hormone, immunodilator, neurotransmitter, receptor, reporter protein, structural protein, and transcription factor.

In one embodiment, the enzyme is an oxidoreductase, transferase, hydrolase, lyase, isomerase, or ligase. In another embodiment, the enzyme is an acetylmannan esterase, acetylxylan esterase, alpha-galactosidase, alpha-glucosidase, alpha-glucuronidase, aminopeptidase, amylase, amyloglucosidase, arabinanase, arabinofuranosidase, beta-galactosidase, beta-glucosidase, beta-xylosidase, carbohydrase, carboxypeptidase, catalase, cellobiohydrolase, cellulase, chitinase, coumaric acid esterase, cutinase, cyclodextrin glycosyltransferase, deoxyribonuclease, endoglucanase, esterase, feruloyl esterase, GH61 polypeptide having cellulolytic enhancing activity, glucocerebrosidase, glucuronidase, hemicellulase, invertase, laccase, lipase, mannanase, mannosidase, mutanase, oxidase, pectinolytic enzyme, peroxidase, phospholipase, phytase, polyphenoloxidase, protease, ribonuclease, transglutaminase, urokinase, or xylanase.

In another aspect, the polypeptide is an albumin, collagen, tropoelastin, elastin, or gelatin.

In another aspect, the polypeptide is an expansin or a swollenin.

In another aspect, the polypeptide is hybrid polypeptide in which a region of one polypeptide is fused at the N-terminus or the C-terminus of a region of another polypeptide.

In another aspect, the polypeptide is a chimeric polypeptide in which one or more (e.g., several) regions of one polypeptide are replaced with one or more (e.g., several) regions from one or more (e.g., several) other polypeptides.

In another aspect, the polypeptide is a fusion polypeptide or cleavable; fusion polypeptide in which one polypeptide is fused at the N-terminus or the C-terminus of another polypeptide. A fusion polypeptide is produced by fusing a polynucleotide encoding the one polypeptide to a polynucleotide encoding the other polypeptide. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The polynucleotide encoding a polypeptide may be obtained from any prokaryotic, eukaryotic, or other source. For purposes of the present invention, the term "obtained from" as used herein in connection with a given source shah mean that the polypeptide is produced by the source or by a cell in which a gene from the source has been inserted.

The techniques used to isolate or clone a polynucleotide encoding a polypeptide are known in the art and include isolation from genomic DNA, preparation from cDNA, or a combination thereof. The cloning of the polynucleotide from such genomic DNA can be effected, e.g., by using the polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the polynucleotide encoding the polypeptide, insertion of the fragment into a vector molecule, and incorporation of the recombinant vector into the fungal cell where multiple copies or clones of the polynucleotide will be replicated. The polynucleotide may be of genomic, cDNA, RNA, semisynthetic, synthetic origin, or any combinations thereof.

Nucleic Acid Constructs

The present invention also relates to nucleic acid constructs comprising a polynucleotide encoding a polypeptide operably linked to a promoter of the present invention and one or more (e.g., several) control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

A polynucleotide may be manipulated in a variety of ways to provide for expression of the polypeptide. Manipulation of the polynucleotide prior to its insertion into a vector may be desirable or necessary depending on the expression vector. The techniques for modifying a polynucleotide utilizing recombinant DNA methods are well known in the art.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos at al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

The present invention also relates to nucleic acid constructs for altering the expression of a gene encoding a polypeptide which is endogenous to a host cell. The constructs may contain the minimal number of components necessary for altering expression of the endogenous gene. In one embodiment, the nucleic acid constructs preferably comprise (a) a targeting sequence, (b) a promoter of the present invention, (c) an exon, and (d) a splice-donor site. Upon introduction of the nucleic acid construct into a cell, the construct inserts by homologous recombination into the cellular genome at the endogenous gene site. The targeting sequence directs the integration of elements (a)-(d) into the endogenous gene such that elements (b)-(d) are operably linked to the endogenous gene. In another embodiment, the nucleic acid constructs comprise (a) a targeting sequence, b) a promoter of the present invention, (c) an exon, (d) a splice-donor site, (e) an intron, and (f) a splice-acceptor site, wherein the targeting sequence directs the integration of elements (a)-(f) such that elements (b)-(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more (e.g., several) targeting sequences can be used. For example, a circular plasmid or DNA fragment preferably employs a single targeting sequence, while a linear plasmid or DNA fragment preferably employs two targeting sequences.

The constructs further contain one or more (e.g., several) exons of the endogenous gene. An exon is defined as a DNA sequence which is copied into RNA and is present in a mature mRNA molecule such that the axon sequence is in-frame with the coding region of the endogenous gene. The exons can, optionally, contain DNA which encodes one or more (e.g., several) amino acids and/or partially encodes an amino acid. Alternatively, the exon contains DNA which corresponds to a 5' non-encoding region. Where the exogenous axon or exons encode one or more (e.g., several) amino acids mod/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

The present invention further relates to methods for producing a polypeptide comprising (a) cultivating a homologously recombinant cell, having incorporated therein a transcription unit comprising a promoter of the present invention, an exon, and/or a splice donor site operably linked to a second exon of an endogenous polynucleotide encoding the polypeptide, under conditions conducive for production of the polypeptide, wherein the polynucleotide encoding the polypeptide is foreign to the promoter; and (b) recovering the polypeptide. The methods are based on the use of gene activation technology, for example, as described in U.S. Pat. No. 5,641,670.

Expression Vectors

The present invention also relates to recombinant expression vectors comprising a promoter of the present invention, a polynucleotide encoding a polypeptide, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide operably linked to a promoter of the present invention or a nucleic acid construct thereof into an appropriate vector for expression. In creating the expression vector, the coding sequence is located in the vector so that the coding sequence is operably linked to a promoter of the present invention.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a promoter of the present invention operably linked to a polynucleotide encoding a polypeptide, which are advantageously used in the recombinant production of the polypeptide. A vector comprising a promoter of the present invention operably linked to a polynucleotide encoding a polypeptide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. Fungi" as used herein includes the phyla Ascomycota, Basidiomycota, Chytridiomycota, and Zygomycota as well as the Oomycota and all mitosporic fungi (as defined by Hawksworth at al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastalicus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth at al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiate, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

The present invention is further described by the following examples which should not be construed as limiting the scope of the invention.

EXAMPLES

Strains

*Aspergillus oryzae* strain #13-1 described in WO 2006/069289 was used as a source of cDNA of the *Trametes cingulata* amyloglucosidase gene (WO 2006/069289).

*Aspergillus nidulans* NRRL 1092 was used as a source of a pyrG gene.

*Aspergillus niger* strain M1010 (NN059095) is a derivative of *Aspergillus niger* NN049184, which was isolated from soil. Strain M1010 is genetically modified to disrupt expression of oxaloacetate hydrolase (oah), pyrG, tripeptidylaminopeptidase, fumonisin, and amyloglucosidase genes and was used as a source of an amyloglucosidase gene terminator.

*Aspergillus niger* 803-2 (a ku70-derivative of an amyloglucosidase producing strain) was used as a source of the cipC promoter.

*Aspergillus niger* 01650 (a pyrG+ version of *A. niger* M1010), which lacks amyloglucosidase (AMG) activity, was used as a negative control.

Media and Solutions

COVE-N-Gly plates were composed of 218 g of sorbitol, 10 g of glycerol, 2.02 g of $KNO_3$, 50 ml of COVE salts solution, 25 g of Noble agar, and deionized water to 1 liter.

COVE salts solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE-N (tf) plates composed of 342.3 g of sucrose, 3 g of $NaNO_3$, 20 ml of COVE salts solution, 30 g of Noble agar, and deionized water to 1 liter.

COVE-N plates were composed of 30 g of sucrose, 3 g of $NaNO_3$, 20 ml of COVE salts solution, 30 g of Noble agar, and deionized water to 1 liter.

COVE-N-JP plates for protoplast regeneration were composed of 342.3 g of sucrose, 20 ml of COVE salt solution, 3 g of $NaNO_3$, 30 g of Noble agar, and deionized water to 1 liter.

YPG medium was composed of 4 g of yeast extract, 1 g of $KH_2PO_4$, 0.5 g of $MgSO_4.7H_2O$, 5 g of glucose, and deionized water to 1 liter (pH 6.0).

YPG+sorbitol medium was composed of 10 g of yeast extract, 20 g of Bacto Peptone, 30 ml of 50% glucose, 20 ml of 2 M sorbitol, and deionized water to 1 liter.

YPG+uridine medium was composed of 10 g of yeast extract, 20 g of Bacto Peptone, 30 ml of 50% glucose, deionized water to 1 liter, and 10 mM uridine.

STC buffer was composed of 0.8 M sorbitol, 25 mM Tris pH 8, and 25 mM $CaCl_2$.

STPC buffer was composed of 40% PEG 4000 in STC buffer.

COVE-N top agarose was composed of 342.3 g of sucrose, 3 g of $NaNO_3$, 20 ml of COVE salts solution, 10 g of low melt agarose, and deionized water to 1 liter.

2× lysis buffer for genomic DNA was composed of 200 mM EDTA, 20 mM Tris pH 8.0, 2% TRITON X-100, 1 M guanidine-HCl, and 400 mM NaCl.

TAE buffer was composed of 4.84 g of Tris base, 1.14 ml of glacial acetic acid, 2 ml of 0.5 M EDTA pH 8.0, and deionized water to 1 liter.

TE buffer was composed of 10 mM Tris Base and 1 mM EDTA, pH 8.0.

EB buffer was composed of 10 mM Tris pH 8.0.

PCR lysis buffer was composed of 400 mM Tris-HCl pH 8.0, 60 mM EDTA pH 8.0, 150 mM NaCl, and 1% SDS.

Potassium acetate pH 4.8 was composed of 60 ml of 5 M potassium acetate, 11.5 ml of glacial acetic acid, and 28.5 ml of deionized water.

MU1/MLC/urea was composed of 1 liter of MU1, 200 ml of MLC, and 40 ml of 50% w/v urea.

MU1 was composed of 260 g of maltodextrin, 3 g of MgSO$_4$.7H$_2$O, 6 g K$_2$SO$_4$, 5 g KH$_2$PO$_4$, 0.5 ml of AMG trace metals solution, three drops of pluronic antifoam, and deionized water to 1 liter; pH adjusted to 4.5.

AMG trace metals solution was composed of 0.3 g citric acid-H$_2$O, 0.68 g ZnCl$_2$, 0.25 g CuSO$_4$.5H$_2$O, 0.024 g NiCl$_2$.6H$_2$O, 1.39 g FeSO$_4$.7H$_2$O, 1.356 g MnSO$_4$.5H$_2$O and deionized water to 1 liter.

MLC was composed of 40 g of glucose, 50 g of soy bean powder, 4 g of citric acid, three drops of pluronic antifoam, and deionized water to 1 liter; pH adjusted to 5.0.

2XYT+amp plates were composed of 16 g of tryptone, 10 g of yeast extract, 5 g of NaCl, 100 mg of ampicillin, and 15 g of bacto agar, and deionized water to 1 liter.

Example 1

Preparation of *Aspergillus Niger* Genomic DNA

Genomic DNA from *Aspergillus niger* strain M1010 was isolated by inoculating 50 ml of YPG+sorbitol medium in a 125 ml shake flask with two approximately 1 cm$^2$ pieces of agar containing spores and mycelia from a densely grown COVE-N-Gly plate of *A. niger* strain M1010 and incubating the flask at 30° C. overnight with shaking at 250 rpm. The mycelia were harvested by filtration using a MIRACLOTH® (Calbiochem, San Diego, Calif., USA) lined funnel. Approximately 2 g of mycelia were recovered, rinsed with 25 ml of 0.6 M KCl, transferred with an inoculating loop to a 50 ml polypropylene conical centrifuge tube containing 10 ml of 0.6 M KCl with 36 mg/ml of GLUCANEX® 200G (Novozymes North America, Franklinton, N.C., USA), and incubated at 37° C. for 1 hour. The tube was centrifuged at 863×g for 5 minutes and the pellet was resuspended in 10 ml of 0.6 M KCl and centrifuged again. The pellet was resuspended in 5 ml of deionized water and incubated at room temperature for 5 minutes. Five ml of 2× lysis buffer were then added. Three µl of 100 mg/ml RNase A (QIAGEN Inc., Valencia, Calif., USA) were added and the tube was incubated at 37° C. for 30 minutes, followed by the addition of 150 µl of 20 mg/ml Proteinase K (QIAGEN Inc., Valencia, Calif., USA) and incubation at 50° C. for 2 hours. The tube was centrifuged at 7240×g for 20 minutes. The supernatant was transferred to a maxi-tip that had been pre-equilibrated in QBT buffer as described in a Plasmid Maxi Kit (QIAGEN Inc., Valencia, Calif., USA) and the remaining DNA extraction steps were performed according to the manufacturer's instructions. The DNA was resuspended in 100 µl of EB buffer.

Example 2

Construction of Plasmid pHUda666

Plasmid pHUda666 was constructed according to the following procedure. Mycelia of *Aspergillus oryzae* strain #13-1 were harvested from an overnight culture, in 100 ml of YPG medium, filtered, rinsed with distilled water, dried, and frozen at −80° C. The RNA sample was prepared using a TRIzol® Plus RNA Purification Kit (Invitrogen, La Jolla, Calif., USA) according to the manufacturer's instructions. Ground mycelia were incubated with 2 ml of TRIzol®, mixed vigorously, and incubated for 5 minutes at room temperature. A 0.4 ml volume of chloroform was added to the mixture and mixed vigorously. A 500 µl volume of the colorless, upper phase containing the RNA was transferred to an RNase-free tube followed by 500 µl of ethanol and mixed. The mixture was transferred to filter tubes supplied with the kit. The tubes were centrifuged at 12,000×g for 1 minute at 4° C. A 700 µl volume of wash solution was added to each tube and then the tubes were centrifuged at 12,000×g for 1 minute at 4° C. Finally the RNA sample was eluted by adding 100 µl of RNase-free water to each tube and centrifuging the tubes at 12,000×g for 1 minute at 4° C.

Primers TCGA-F and TCAG-R, shown below, were designed to amplify cDNA of the *Trametes cingulata* amyloglucosidase gene by PCR based on the polynucleotide sequence information in WO 2006/069289.

```
TCGA-F (sense):
                                    (SEQ ID NO: 9)
5'-TGGGGGATCCACCATGCGTTTCACGCTCCT-3'

TCCA-R (anti-sense):
                                    (SEQ ID NO: 10)
5'-CTCGAGTTAATTAACTACCGCCAGGTGTCGTTC-3'
```

The amplification reaction (50 µl) was composed of 1 ng of total RNA per µl, 250 mM dNTP each, 250 nM primer TCGA-F, 250 nM primer TCGA-R, 1 unit of RNase inhibitor (Roche Diagnostics, Japan), 0.1 unit of reverse transcriptase (Roche Diagnostics, Japan), 10 µl of 1× buffer (Roche Diagnostics, Japan), and 0.1 unit of Taq DNA polymerase (Roche Diagnostics, Japan) per µl of 1× buffer. The reactions were incubated in a DNA Engine PTC-200 (MJ-Research, Japan) programmed for 1 cycle at 50° C. for 30 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated by 1.0% agarose gel electrophoresis using TAE buffer where a 1.7 kb product band was excised from the gel and purified using a QIAQUICK™ Gel Extraction Kit (QIAGEN Inc., Valencia, Calif., USA) according to the manufacturer's instructions.

The 1.7 kb amplified DNA fragment was digested with Bam HI and Xho I, and ligated into the *Aspergillus* expression cassette pJaL790 (WO 2005/070962) digested with Bam HI and Xho I using a Rapid Dephos and Ligation Kit (Roche Applied Science, Indianapolis, Ind., USA) according to the manufacturer's instructions in a total reaction volume of 21 µl composed of 2 µl of buffer 3, 10 µl of buffer 4, 200 ng of the recovered 1.7 kb fragment, 100 ng of pJaL790 Bam HI and Xho I digested vector fragment, and 1 µl of ligase. The buffers and ligase with supplied with the kit. The reaction was incubated at room temperature for 30 minutes. A 10 µl aliquot of the ligation reaction above was transformed into chemically competent cells of *E. coli* DB6507. Plasmid pHUda666 was recovered using a QIAPREP® Spin Miniprep Kit (QIAGEN Inc., Valencia, Calif., USA) according to the manufacturer's instructions.

Plasmid pJaL790 comprises an expression cassette based on three copies of the *Aspergillus niger* neutral amylase II promoter linked in the same direction, the *Aspergillus nidulans* triose phosphate isomerase non-translated leader sequence fused to the last *Aspergillus niger* neutral amylase II promoter (triple Na2/tpi promoter), the *Aspergillus niger* amyloglycosidase terminator (AMG terminator), and the selective marker amdS from *Aspergillus nidulans* allowing growth on acetamide as sole nitrogen source.

Example 3

Cloning of the *Aspergillus Nidulans* pyrG Gene Fused with the *Aspergillus Niger* Amyloglucosidase Terminator to Form pHUda794

Plasmid pHUda794 was constructed according to the following procedure. Primers nidP-f and nidP-r1, as shown below, were designed to amplify the *A. nidulans* pyrG gene by PCR based on the polynucleotide sequence information in the genome database of *A. nidulans* NRRL 1092 (Galagan et al., 2005, *Nature* 438: 1105-1115. Primer nidP-f introduces a Spe I site.

```
nidP-f (sense):
                                      (SEQ ID NO: 11)
5'-TTTGCTAGCACTAGTTACTAAATGACGTTTGTGAAC-3' nidP-r1 (anti-sense):
                                      (SEQ ID NO: 12)
5'-CTACCGCCAGGTGTCAGTCACCCTCAAAGTCCAACTCTTT-3'
```

A PCR reaction with the genomic DNA of *A. nidulans* NRRL 1092 as template was performed with an EXPAND™ PCR System (Roche Diagnostics, Japan) and primers nidP-f and nidP-r1 Mycelia of *A. nidulans* NRRL 1092 were harvested from an overnight culture in 100 ml of YPG plus uridine medium, filtered, rinsed with distilled water, dried, and frozen at −80° C. Ground mycelia were incubated with Proteinase K and RNase A (QIAGEN Inc., Valencia, Calif., USA) at 65° C. for 1 hour. Genomic DNA was recovered by phenol/CHCl$_3$/isoamylalcohol (25:24:1 v/v/v) extraction twice followed by ethanol precipitation and resuspension in distilled water.

The amplification reaction (50 µl) was composed of 1 ng of *A. nidulans* NRRL 1092 genomic DNA per µl, 250 mM dNTP each, 250 nM primer nidP-F, 250 nM primer nidP-r1, 10 µl of 1× buffer, and 0.1 unit of Taq DNA polymerase per µl of 1× buffer. The reactions were incubated in a DNA Engine PTC-200 programmed for 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated by 1.0% agarose gel electrophoresis using TAE buffer where a 1.4 kb product band was excised from the gel and purified using a QIAQUICK® Gel Extraction Kit according to the manufacturer's instructions.

Primers nidP-f1 and nigGAT-r, shown below, were designed to amplify the *A. niger* amyloglucosidase terminator region by PCR based on the polynucleotide sequence information in the genome database of *A. niger* CBS 513.88 (Pel et al., 2007, *Nature Biotechnology* 25: 221-231).

```
nidP-f1 (sense):
                                      (SEQ ID NO: 13)
5'-AAAGAGTTGGACTTTGAGGGTGACTGACACCTGGCGGTAG-3' nigGAT-r (anti-sense):
                                      (SEQ ID NO: 14)
5'-TCTCTAGAGGAGAGAGTTGAACCTGGACGC-3'
```

A PCR reaction with the genomic DNA of *A. niger* M1010 as template was performed with an EXPAND™ PCR System and primers nidP-f1 and nigGAT-r. Mycelia of *A. niger* M1010 were harvested from an overnight culture in 100 ml of YPG plus uridine medium, filtered, rinsed with distilled water, dried, and frozen at −80° C. Ground mycelia were incubated with Proteinase K and RNase A at 65° C. for 1 hour. Genomic DNA was recovered by phenol/CHCl$_3$/isoamylalcohol (25:24:1 v/v/v) extraction twice followed by ethanol precipitation and resuspension in distilled water.

The amplification reaction (50 µl) was composed of 1 ng of *A. niger* M1010 genomic DNA per µl, 250 mM dNTP each, 250 nM primer nidP-F1, 250 nM primer nigGAT-r, 10 µl of 1× buffer, and 0.1 unit of Taq DNA polymerase per µl of 1× buffer. The reactions were incubated in a DNA Engine PTC-200 programmed for 1 cycle at 94° C. for 2 minutes; 30 cycles each at 92° C. for 1 minute, 55° C. for 1 minute, and 72° C. for 1 minute; 1 cycle at 72° C. for 10 minutes; and a hold at 4° C.

The reaction products were isolated by 1.0% agarose gel electrophoresis using TAE buffer where a 0.7 kb product band was excised from the gel and purified using a QIAQUICK® Gel Extraction Kit according to the manufacturer's instructions.

A PCR reaction with the purified 1.4 kb fragment containing the *A. nidulans* pyrG gene and the purified 0.7 kb fragment containing the *A. niger* amyloglucosidase terminator was performed with an EXPAND™ PCR System using primers nidP-f and nigGAT-r. The amplification reaction (50 µl) was composed of 1 ng of the 1.4 kb fragment containing the *A. nidulans* pyrG gene and 1 ng of the 0.7 kb fragment containing the *A. niger* amyloglucosidase terminator per µl, 250 mM dNTP each, 250 nM primer nidP-F, 250 nM primer nidP-R, 10 µl of 1× buffer, and 0.1 unit of Taq DNA polymerase per µl of 1× buffer. The reactions were incubated in a DNA Engine PTC-200 programmed for 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated by 1.0% agarose gel electrophoresis using TAE buffer where a 2.1 kb product band was excised from the gel and purified using a QIAQUICK® Gel Extraction Kit according to the manufacturer's instructions.

The 2.1 kb amplified DNA fragment was cloned into pCR02.1-TOPO® (Invitrogen, La Jolla, Calif., USA) using a TOPO® Cloning Kit (Invitrogen, La Jolla, Calif., USA) according to the manufacturer's protocol in a total reaction volume of 6 µl composed of 1 µl of salt solution, 50 ng of the recovered 2.1 kb fragment, and 1 µl of pCR®2.1-TOPO®. The reaction was incubated at room temperature for 30 minutes. A 5 µl aliquot of the TOPO reaction above was transformed into chemically competent *E. coli* cells DH5α (TOYOBO, Japan) according to the manufacturer's instructions to create the plasmid pHUda794.

Example 4

Construction of Plasmid pHUda798

Plasmid pHUda798 was constructed according to the following procedure. Plasmid pHUda794 was digested with Spe I and Xba I to generate a 2.1 kb DNA fragment containing the *A. nidulans* pyrG gene fused to the *A. niger* amyloglucosidase terminator, which was recovered using a QIAQUICK™ Gel Extraction Kit according to the manufacturer's instructions. The recovered 2.1 kb fragment was ligated to Xba I digested pHUda666 using a Rapid Dephos and Ligation Kit according to the manufacturer's instructions in a total reaction volume of 21 µl composed of 2 µl of buffer 3, 10 µl of buffer 4, 200 ng of the recovered 2.1 kb fragment, 100 ng of the Xba I digested pHUda666 fragment, and 1 µl of ligase. The reaction was incubated at room temperature for 30 minutes. A 10 µl aliquot of the ligation reaction above was transformed into chemically competent *E. coli* cells DH5α, cells according to the manufacturer's instructions to create plasmid pHUda798. Plasmid pHUda798 was recovered using a QIAPREP® Spin Miniprep Kit according to the manufacturers instructions.

Plasmid pHUda798 comprises an expression cassette of the *T. cingulata* amyloglucosidase gene based on three copies of the *A. niger* neutral amylase II promoter linked in the same direction, the *A. nidulans* triose phosphate isomerase non-translated leader sequence fused to the last *A. niger* neutral amylase II promoter (triple Na2/tpi promoter), the *A. niger* amyloglycosidase terminator (AMG terminator), and the selective marker pyrG with *A. niger* AMG terminator repeats.

Example 5

Construction of Plasmid pTK2

Plasmid pTK2 was constructed according to the following procedure. Plasmid pJaL574 (WO 2007/045248, Example 9) was digested with Eco RI and Xho I to generate a 2.5 kb DNA fragment containing the Herpes simplex virus (HSV) thymidine kinase gene (TK), which was recovered using a QIAQUICK™ Gel Extraction Kit according to the manufacturer's instructions. The recovered 2.5 kb fragment was ligated to Eco RI and Xho I digested pBluescript® II SK— (Agilent Technologies, Santa Clara, Calif., USA; Genbank #X52330) using a Rapid Dephos and Ligation Kit according to the manufacturer's instructions in a total reaction volume of 21 µl composed of 2 µl of buffer 3, 10 µl of buffer 4, 200 ng of the recovered 2.5 kb fragment, 100 ng of the Eco RI and Xho I digested pBluescript® II SK-fragment, and 1 µl of ligase. The reaction was incubated at room temperature for 30 minutes. A 10 µl aliquot of the ligation reaction above was transformed into chemically competent *E. coli* cells DH5α cells according to the manufacturer's instructions to create plasmid pTK2. Plasmid pTK2 was recovered using a QIAprep® Spin Miniprep Kit according to the manufacturer's instructions.

Example 6

Construction of Plasmid pTK2-5NA1

Plasmid pTK2-5NA1 was constructed according to the following procedure. Primers 5NA1F2 and 5NA1R2, shown below, which introduce a Not I site and Nhe I/Xba I sites, respectively, were designed to amplify the *A. niger* strain M1010 5' flanking region of the neutral amylase I (NAI) gene based on the polynucleotide sequence information in the genome database of *A. niger* CBS 513.88 (Pel et al., 2007, supra).

```
5NA1F2 (sense):
                                      (SEQ ID NO: 15)
5'-GGCGGCCGCGTTTAAACCTATCTGTTCCC-3'

5NA1R2 (anti-sense):
                                      (SEQ ID NO: 16)
5'-TCGTCTAGAGCTAGCTGACTTCTATATAAAAATGAGT-3'
```

A PCR reaction with *A. niger* M1010 genomic DNA (Example 3) as template was performed with an EXPAND™ PCR System and primers 5NA1F2 and 5NA1R2.

The amplification reaction (50 µl) was composed of 1 ng of *A. niger* M1010 genomic DNA per µl, 250 mM dNTP each, 250 nM primer 5NA1F, 250 nM primer 5NA1R, 10 µl of 1× buffer, and 0.1 unit of Taq DNA polymerase per µl of 1× buffer. The reactions were incubated in a DNA Engine PTC-200 programmed for 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated by 1.0% agarose gel electrophoresis using TAE buffer where a 1.8 kb product band was excised from the gel and purified using a QIAQUICK® Gel Extraction Kit according to the manufacturer's instructions.

The 1.8 kb amplified DNA fragment was digested with Not I and Xba I, and ligated to Not I and Xba I digested pTK2 using a Rapid Dephos and Ligation Kit according to the manufacturer's instructions in a total reaction volume of 21 µl composed of 2 µl of buffer 3, 10 µl of buffer 4, 200 ng of the recovered 1.8 kb fragment, 100 ng of the Not I and Xba I digested pTK2 Xba I fragment, and 1 µl of ligase. The reaction was incubated at room temperature for 30 minutes. A 10 µl aliquot of the ligation reaction above was transformed into chemically competent *E. coli* cells DH5α according to the manufacturer's instructions to create plasmid pTK2-5NA1. Plasmid pTK2-5NA1 was recovered using a QIAPREP® Spin Miniprep Kit according to the manufacturer's instructions.

Example 7

Construction of Plasmid pTK2-5NA1-3NA1

Plasmid pTK2-5NA1-3NA1 was constructed according to the following procedure. Primers 3NA1F2 and 3NA1R2, shown below, which introduce an Xba I site and an Eco RI site, respectively, were designed to amplify the *A. niger* strain M1010 3' flanking region of the neutral amylase I (NAI) gene based on the polynucleotide sequence information in the genome database of *A. niger* CBS 513.88 (Pel et al., 2007, supra).

```
3NA1F2 (sense):
                                      (SEQ ID NO: 17)
5'-TCCTCTAGAGTATATGATGGTACT-3'

3NA1R (anti-sense):
                                      (SEQ ID NO: 18)
5'-GGAGAATTCTTAATTAAGCATTCTCCTAGTTACT-3'
```

A PCR reaction with *A. niger* M1010 genomic DNA (Example 3) as template was performed using an EXPAND™ PCR System using primers 3NA1F2 and 3NA1R2. The amplification reactions (50 µl) were composed of 1 ng of *A. niger* M1010 genomic DNA per µl, 250 mM dNTP each, 250 nM primer 3NA1F, 250 nM primer 3NA1R, 10 µl of 1× buffer, and 0.1 unit of Taq DNA polymerase per µl of 1× buffer. The reactions were incubated in a DNA Engine PTC-200 programmed for 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated by 1.0% agarose gel electrophoresis using TAE buffer where a 1.4 kb product band was excised from the gel and purified using a QIAQUICK® Gel Extraction Kit according to the manufacturer's instructions.

The 1.4 kb amplified DNA fragment was digested with Xba I and Eco RI, and ligated to Xba I and Eco RI digested pTK2-5NA1 using a Rapid Dephos and Ligation Kit according to the manufacturer's instructions in a total reaction volume of 21 µl composed of 2 µl of buffer 3, 10 µl of buffer 4, 200 ng of the recovered 1.4 kb fragment, 100 ng of pTK2-5NA1 Xba I and Eco RI digested vector fragment, and 1 µl of ligase. The reaction was incubated at room temperature for 30 minutes. A 10 µl aliquot of the ligation reaction above was transformed into chemically competent *E. coli* cells DH5α cells according to the manufacturer's instructions to create plasmid pTK2-5NA1-3NA1. Plasmid pTK2-5NA1-3NA1 was recovered using a QIAprep® Spin Miniprep Kit according to the manufacturer's instructions.

Example 8

Construction of Plasmid pHUda852

Plasmid pHUda852 was constructed as the *A. niger* triple NA2 promoter driven *T. cingulata* amyloglucosidase reporter plasmid for site-specific integration at the *A. niger* NA1 locus.

Plasmid pHUda798 was digested with Nhe I and Xba I to generate a 6.1 kb DNA fragment containing the *T. cingulata* amyloglucosidase expression cassette and the *A. nidulans* pyrG gene, which was recovered using a QIAQUICK™ Gel Extraction Kit according to the manufacturer's instructions. The recovered 6.1 kb fragment was ligated to Xba I digested pTK2-5NA1-3NA1 using a Rapid Dephos and Ligation Kit according to the manufacturer's instructions in a total reaction volume of 21 µl composed of 2 µl of buffer 3, 10 µl of buffer 4, 200 ng of the recovered 6.1 kb fragment, 100 ng of pTK2-5NA1-3NA1 Xba I vector fragment, and 1 µl of ligase. The reaction was incubated at room temperature for 30 minutes. A 10 µl aliquot of the ligation reaction above was transformed into chemically competent *E. coli* cells DH5α cells according to the manufacturer's instructions to create expression plasmid pHUda852 (FIG. 1). Plasmid pHUda852 was recovered using a QIAPREP® Spin Miniprep Kit according to the manufacturer's instructions.

Plasmid pHUda852 comprises an expression cassette of the *T. cingulata* amyloglucosidase gene based on three copies of the *A. niger* neutral amylase II promoter linked in the same direction, the *A. nidulans* triose phosphate isomerase non-translated leader sequence fused to the last *A. niger* neutral amylase II promoter (triple Na2-tpi promoter) and the *A. niger* amyloglycosidase terminator (AMG terminator), the selective marker pyrG from *A. nidulans* with AMG terminator, the H. simplex virus (HSV) thymidine kinase gene between the *A. nidulans* glycerol phosphate dehydrogenase (gpd) promoter and the terminator of the *A. nidulans* trpC gene, which is involved in tryptophan biosynthesis, and 5' and 3' flanking regions of the *A. niger* neutral amylase I gene.

Example 9

Construction of pMhCt036, an *Aspergillus Niger* cipC Promoter Driven *Trametes Cingulata* Amyloglucosidase Reporter Plasmid for Site-Specific Integration at the *A. Niger* NA1 Locus To determine the expression potential from the *A. niger* concanamycin-induced protein C gene (cipC) promoter, a plasmid was constructed to target a reporter protein, *T. cingulata* amyloglucosidase, under control of the cipC promoter (SEC) ID NO: 1) to the NA1 locus of *A. niger*. A PCR fragment containing 5' homology to the Nhe I site region of pHUda852, −1008 to −3 of the promoter region from the *A. niger* cipC gene plus a 12 base pair linker followed by +1 to +8 of the *T. cingulata* amyloglucosidase open reading frame was generated from *A. niger* strain 803-2 genomic DNA (prepared according to the procedure described in Example 1) using the following primers:

```
Primer 065879 (sense):
                                          (SEQ ID NO: 19)
5'-TTATATAGAAGTCAGCTAGCCAAGACGAGAAGCTGACCG-3'
                 Nhe I Primer 065880 (anti-sense):
                                          (SEQ ID NO: 20)
5'-AAACGCATGGTGGATCCCCCGATTGATGTATGAAGTAGTGAAGAG-3'
              Bam HI
```

The PCR reaction (50 µl) was composed 100 ng of *A. niger* strain 803-2 genomic DNA (prepared according to Example 1), 1× Proof™ HF buffer (Bio-Rad Laboratories, Inc., Hercules, Calif., USA), 100 pmol of primer 065879, 100 pmol of primer 065880, 200 µM each of dATP, dCTP, dGTP, and dTTP, and 1 unit of iProof™ High Fidelity DNA polymerase (Bio-Rad Laboratories, Inc., Hercules, Calif., USA). The PCR was performed in an EPPENDORF® MASTERCYCLER® (Eppendorf AG, Hamburg, Germany) programmed for 1 cycle at 98° C. for 30 seconds followed by 32 cycles each at 98° C. for 10 seconds, 53° C. for 30 seconds, and 72° C. for 30 seconds. The final extension cycle was at 72° C. for 5 minutes. Following thermocycling, the PCR reaction products were separated by 0.9% agarose gel electrophoresis using TAE buffer where an approximately 1 kb PCR product was excised from the gel and purified using a NUCLEOSPIN® Extract II Kit (Macherey-Nagel, Bethlehem, Pa., USA) according to the manufacturer's instructions.

A second PCR fragment containing 5' homology to the PCR product above including the Bam HI site, a 12 base pair linker, and +1 to +386 of the *T. cingulata* amyloglucosidase open reading frame (a Stu I site lies at the +366 to +371 position) was generated by PCR from pHUda852 plasmid DNA using the following primers:

```
Primer 065881 (sense):
                                          (SEQ ID NO: 21)
5'-CTCTTCACTACTTCATACATCAATCGGGGGATCCACCATGCGTTT-
3'
                                    Bam HI
Primer 065882 (anti-sense):
                                          (SEQ ID NO: 22)
5'-AACTTGGGCTCGCCGAGG-3'
```

(Half of the endogenous Stu I site is contained in this primer and is underlined above.)

The PCR reaction (50 µl) was composed of 10 ng of pHUda852, 1× cloned Pfu DNA polymerase buffer (Agilent Technologies, Santa Clara, Calif., USA), 100 pmol of primer 065881, 100 pmol of primer 065882, 200 µM each of dATP, dCTP, dGTP, and dTTP, and 2.5 units Pfu TURBO® DNA polymerase (Agilent Technologies, Santa Clara, Calif., USA). The PCR was performed in an EPPENDORF® MASTERCYCLER® programmed for 1 cycle at 94° C. for 2 minutes followed by 32 cycles each at 94° C. for 30 seconds, 50° C. for 30 seconds, and 72° C. for 1 minute. The final extension cycle was at 72° C. for 5 minutes. Following thermocycling, the PCR reaction was separated by 0.9% agarose gel electrophoresis using TAE buffer where an approximately 400 bp PCR product was excised from the gel and purified using a NUCLEOSPIN® Extract II Kit according to the manufacturer's instructions.

Plasmid pHUda852 was digested with Nhe I and Stu I and purified by 0.9% agarose gel electrophoresis using TAE buffer where an approximately 12.7 kb band was excised from the gel and purified using a NUCLEOSPIN® Extract II Kit according to the manufacturer's instructions.

Figure 2:
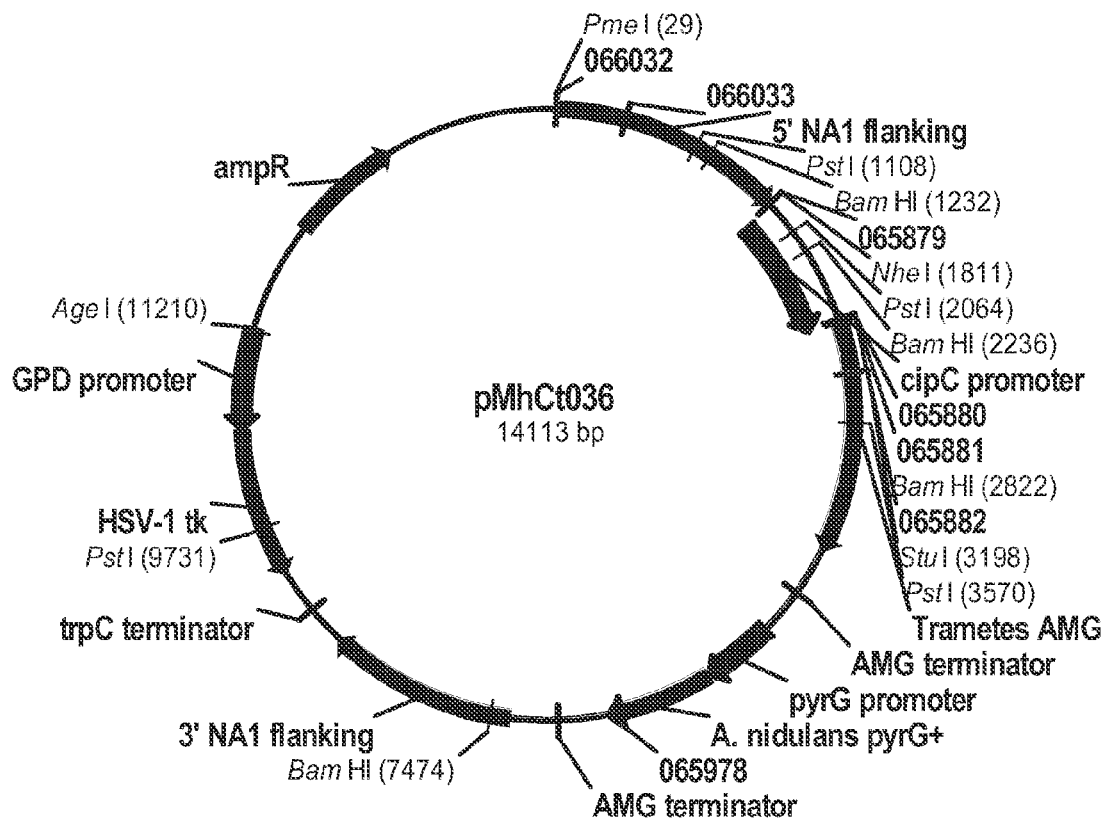
FIG. 2 shows a restriction map of pMhCt036.

The purified 400 bp and 12.7 kb PCR products above were then inserted into the Nhe I/Stu I digested pHUda852 fragment using an IN-FUSION™ PCR Cloning Kit (Clontech, Mountain View, Calif., USA) in a total reaction volume of 20 µl composed of 2 µl of 10× buffer (Clontech, Mountain View, Calif., USA), 2 µl of 10×BSA (Clontech, Mountain View, Calif., USA), 200 ng of each PCR product, 100 ng of the Nhe I/Stu I digested pHUda852 fragment, and 1 µl of IN-FUSION™ enzyme (Clontech, Mountain View, Calif., USA). The reaction was incubated at 42° C. for 30 minutes, placed on ice, and diluted with 40 µl of TE buffer. A 4 µl aliquot of the ligation reaction was transformed into ONE SHOT® TOP10 chemically competent *E. coli* cells (Invitrogen, San Diego, Calif., USA) according to the manufacturer's instructions. Transformants were plated onto 2XYT+amp plates and incubated at 37° C. overnight. Several of the resulting transformants were screened for proper insertion of the desired PCR products by Pst I digestion. A clone yielding the desired band sizes was confirmed to be correct by DNA sequencing and designated pMhCt036 (FIG. 2).

Plasmid pMhCt036 comprises an expression cassette of the *T. cingulata* amyloglucosidase gene under transcriptional control of the cipC promoter and the *A. niger* amyloglycosidase terminator (AMG terminator), the selective marker pyrG from *A. nidulans* with the *A. niger* amyloglycosidase terminator (AMG terminator), the Herpes simplex virus (HSV) thymidine kinase gene between the *A. nidulans* glycerol phosphate dehydrogenase (gpd) promoter and terminator of the *A. nidulans* trpC gene, and 5' and 3' flanking regions of the *A. niger* neutral amylase I.

Example 10

Construction of *Aspergillus Niger* 889-852-47

*Aspergillus niger* 889-852-47 was constructed, as described below, as a control strain for comparison of the triple NA2-tpi promoter to the cipC promoter.

*A. niger* strain M1010 was inoculated into 100 ml of YPG uridine medium and incubated for 16 hours at 32° C. and 80 rpm. Pellets were collected and washed with 0.6 M KCl, and resuspended in 20 ml of 0.6 M KCl containing GLUCANEX™ (Novozymes A/S, Bagsvaerd, Denmark) at a final concentration of 20 mg per mi. The suspension was incubated at 32° C. and 80 rpm until protoplasts were formed, and then washed twice with STC buffer. The protoplasts were counted with a hemacytometer (VWR, West Chester, Pa., USA) and resuspended and adjusted in an 8:2:0.1 v/v/v solution of STC: STPC:DMSO to a final concentration of $2.5 \times 10^7$ protoplasts/ml. Approximately 3 µg of pHUda852 were added to 100 µl of the protoplast suspension, mixed gently, and incubated on ice for 30 minutes. One ml of SPTC was added and the protoplast suspension was incubated for 20 minutes at 37° C. After the addition of 10 ml of 50° C. COVE-N top agarose, the reaction was poured onto COVE-N (tf) plates and the plates were incubated at 32° C. After 5 days, transformants were selected from the COVE-N (tf) medium.

Randomly selected transformants were inoculated onto COVE-N plates supplemented with 2.5 µM 5-fluoro-2-deoxyuridine (FdU), an agent which kills cells expressing the H. simplex virus (HSV) thymidine kinase gene (TK) harbored in pHUda852. Strains that grew well on COVE-N plates with 2.5 µM FdU were purified by single colony isolation and subjected to Southern blot analysis to confirm if the expression cassette in pHUda852 was correctly integrated at the NA1 (neutral amylase I) locus as described below.

Mycelia of the selected transformants were harvested from overnight cultures in 100 ml of YPG plus mM uridine medium, filtered, rinsed with distilled water, dried, and frozen at −80° C. Ground mycelia were incubated with Proteinase K and RNase A at 65° C. for 1 hour. Genomic DNA was recovered by phenol/CHCl$_3$ (25:24:1 v/v/v) extraction twice followed by ethanol precipitation and resuspension in distilled water.

Non-radioactive probes were synthesized using a PCR DIG Probe Synthesis Kit (Roche Applied Science, Indianapolis, Ind., USA) according to the manufacturer's instructions. DIG labeled probes were gel purified using a QIAQUICK™ Gel Extraction Kit according to the manufacturer's instructions. A NA1 locus specific probe was prepared using the primers shown below to amplify by PCR an approximately 500 bp 5' NA1 region from the *A. niger* NA1 locus.

```
NA1 forward primer (sense):
                                    (SEQ ID NO: 23)
5'-AATCCGGATCCTTTCCTATA-3'

NA1 reverse primer (anti-sense):
                                    (SEQ ID NO: 24)
5'-GATGGAGCGCGCCTAGAAGC-3'
```

The PCR (100 µl) was composed of 1× EXPAND™ buffer (Roche Diagnostics, Japan), 50 pmol of NA1 forward primer, 50 pmol of NA1 reverse primer, 200 µM DIG dNTP mixture, 5 units of EXPAND™ DNA polymerase (Roche Diagnostics, Japan), and 100 ng of pHUda852. The PCR was performed in an EPPENDORF® MASTERCYCLER® programmed for 1 cycle at 95° C. for 2 minutes followed by 30 cycles each at 95° C. for 30 seconds, 60° C. for 30 seconds, and 72° C. for 30 seconds. The final extension cycle was at 72° C. for 10 minutes. Following thermocycling, the PCR reaction was separated by 1.0% agarose gel electrophoresis using TAE buffer where a 500 bp band was excised from the gel and purified using a QIAQUICK™ Gel Extraction Kit according to the manufacturer's instructions.

A *T. cingulata* amyloglucosidase specific probe was prepared using the primers shown below to amplify by PCR an approximately 500 bp region from the *A. niger* NA1 locus.

```
AMG forward primer (sense):
                                    (SEQ ID NO: 25)
5'-TGATTGCAAGTCCGAGCACA-3'

AMG reverse primer (anti-sense):
                                    (SEQ ID NO: 26)
5'-GAGGTTTGTCCGATGCGATT-3'
```

The PCR (100 µl) was composed of 1× EXPAND™ buffer, 50 pmol of AMG forward primer, 50 pmol of AMG reverse primer, 200 µM DIG dNTP mixture, 5 units of EXPAND™ DNA polymerase, and 100 ng of pHUda852. The PCR was performed in an EPPENDORF® MASTERCYCLER® programmed for 1 cycle at 95° C. for 2 minutes followed by 30 cycles each at 95° C. for 30 seconds, 60° C. for 30 seconds, and 72° C. for 30 seconds. The final extension cycle was at 72° C. for 10 minutes. Following thermocycling, the PCR reaction was separated by 1.0% agarose gel electrophoresis using TAE buffer where a 500 bp band was excised from the gel and purified using a QIAQUICK™ Gel Extraction Kit according to the manufacturer's instructions.

Five micrograms of genomic DNA from randomly selected strains that grew well on COVE-N plates with 2.5 µM FdU were digested with Nco I or Nhe I/Spe I and submitted to 0.8% agarose gel electrophoresis using TAE buffer. The DNA was fragmented in the gel by treatment with 0.2 M HCl for 20 minutes, denatured with 0.5 M NaOH-1.5 M NaCl for 30 minutes, and neutralized with 1 M Tris pH 7.5-1.5 M NaCl for 30 minutes, for subsequent transfer in 20×SSC to a HYBOND™ N+ membrane (Amersham, GE Healthcare, Piscataway, N.J., USA). The DNA was UV cross-linked to the membrane and prehybridized for 1 hour at 42° C. in 20 ml of DIG Easy Hyb buffer (Roche Diagnostics, Japan). The denatured probe was added directly to the DIG Easy Hyb buffer and hybridization was performed overnight at 42° C. Following post-hybridization washes (twice in 2×SSC at room temperature for 5 minutes and twice in 0.1×SSC at 68° C. for 15 minutes each), chemiluminescent detection using the DIG detection system and CPD-STAR® reagent (Roche Diagnostics, Japan) was performed according to the manufacturer's protocol. DIG-labeled DNA Molecular Weight Marker II (Roche Diagnostics, Japan) was used as standard markers.

The correct integration event resulted in a shifting of a hybridized signal at 2.8 kb by Nco I digestion to 4.6 kb probed with the 5' NA1 flanking region, while a 6.4 kb Nhe I/Spe I digested band was detected with the amyloglucosidase probe. Among the strains with the correct integration event, one strain was chosen and designated *A. niger* 889-852-47.

Example 11

Transformation of pMhCt036 into *Aspergillus Niger* M1010

Protoplast preparation of *A. niger* M1010 was performed by inoculating approximately 2×10$^7$ spores into a 250 ml flask containing 100 ml of YPG+uridine medium and incubating the flask at 32° C. for 16-18 hours at 200 rpm. Mycelia were collected by pouring the culture through a sterile funnel lined with MIRACLOTH® and rinsing with 50 ml of 0.6 M KCl. The washed mycelia were resuspended in a 125 ml flask containing 20 ml of protoplasting solution composed of 20 mg of GLUCANEX® 200 G per ml of 0.6 M KCl and incubated at 32° C. for 1 hour with mixing at 80 rpm. The protoplasting solution was poured through a sterile funnel lined with MIRACLOTH® and rinsed with 50 ml of 0.6 M KCl. The flow-through was collected in two 50 ml polypropylene tubes. The tubes were centrifuged at 1300×g for 5 minutes at room temperature. The supernatant was discarded and the protoplast pellets were combined via re-suspension in a total of 20 ml of STC buffer. A 10 µl sample of the suspension was removed and the protoplasts were counted by a hemacytometer. The remaining protoplast suspension was centrifuged at 1300×g for 5 minutes at room temperature and the pellet was resuspended to a final concentration of 1×10$^7$ protoplasts/ml in a solution containing a ratio of 8:2:0.1 v/v/v STC/SPTC/DMSO. The protoplast solution was then aliquoted to 1.8 ml cryovials (Nunc, Thermo Scientific, Rochester, N.Y., USA) and frozen to –80° C. in a Mr. Frosty freezing container (NALGENE, Thermo Scientific, Rochester, N.Y., USA).

Plasmid pMhCt036 was prepared for transformation by restriction digestion with Pme I and Age I. An 11,181 bp fragment containing the expression cassette, the NA1 flanking regions, the pyrG selection marker, and the H. simplex virus thymidine kinase (HSV-1 TK) counter-selectable marker was separated from the vector fragment by 0.9% agarose gel electrophoresis using TAE buffer, excised from the gel, and purified using a NUCLEOSPIN® Extract II Kit according to the manufacturer's instructions. Two transformation reactions were prepared. For each reaction, a 100 µl solution of protoplast preparation (thawed on ice) was transferred to a 14 ml polypropylene tube to which were added 1.5 µg of the purified Pme I and Age I digested pMhCt036 fragment. The protoplast and DNA solution was incubated on ice 30 minutes. Then 1 ml of SPTC was added and mixed gently, followed by incubation at 37° C. for 20 minutes. A 12.5 ml volume of 50° C. molten COVE-N top agarose was added to each transformation reaction and the resulting suspensions were poured to top coat COVE-N-JP plates for protoplast regeneration. Plates were incubated at 30° C. until colonies appeared four days later.

Example 12

Screening of pMhCt036 Transformants for Proper Integration at the NA1 Locus

Fifty transformants from the original transformation plates (Example 11) were picked to independent COVE-N-Gly plates and allowed to grow at 30° C. To screen for strains lacking the HSV-1 TK counter-selectable marker, a sterile toothpick was used to move a small amount of each transformant to a well of a 24-well microtiter tray (BD Biosciences, Bedford, Mass., USA) containing 1.5 ml of COVE-N-Gly agar plus 5 µM 5-fluoro-2-deoxyuridine (FdU). After one week at 30° C., twelve transformants that grew robustly on the FdU plates were chosen for further analysis. Spores from the originally isolated COVE-N-Gly plate were streaked onto new COVE-N-Gly plates to isolate colonies. After two days of growth at 30° C., a single isolated colony was picked from each plate to a new COVE-N-Gly plate and grown at 30° C. until sporulated. This spore purification procedure was repeated to yield double spore purified transformants.

To allow PCR screening for the desired single copy integrants targeted to the NA1 locus, small-scale genomic DNA preparations from twelve potential integrants were made as follows. Two plugs containing spores, mycelia, and agar for each potential integrant were transferred from the COVE-N-Gly plates to 1.5 ml tubes using a sterile disposable transfer pipet (VWR, West Chester, Pa., USA). Then 500 µl of PCR lysis buffer and approximately 100 µl of 0.5 mm zirconia/silica beads (BioSpec Products, Bartlesville, Okla., USA) were then added to each tube. Cells were disrupted by two rounds of agitation in a FASTPREP® FP120A machine (Qbiogene, Inc, Carlsbad, Calif., USA) at a setting of 4.5 for 45 seconds. The tubes were centrifuged at 16,100×g for 1 minute followed by addition of 150 µl of potassium acetate pH 4.8. The tubes were vortexed briefly. Following a second centrifugation at 16,100×g for 1 minute, 400 µl of the supernatants were transferred to new tubes. To remove residual solids, the centrifugation was repeated and the supernatants were transferred to 1.5 ml tubes. A 400 µl volume of isopropanol was added to each tube and then inverted to mix. The tubes were centrifuged at 16,100×g for 5 minutes and the supernatants were discarded. The pellets were washed with 500 µl of 70% ethanol. After a final centrifugation for 1 minute at 16,100×g, the supernatants were removed and the pellets were dried for 5 minutes in a Savant ISS110 SpeedVac Concentrator (Thermo Scientific, Rochester, N.Y., USA). Pellets were resuspended in 50 µl of TE.

The primers shown below were designed to differentiate the NA1 locus in the *A. niger* M1010 parent strain from the desired pMhCt036 modified locus. Primer 065978 anneals at the end of the pyrG+ open reading frame, while primer 065979 anneals in the *A. niger* genome just 3' of the NA1 flanking region contained in pMhCt036:

```
065978 (sense):
                                    (SEQ ID NO: 27)
5'-GTTGGGCGAGGTGCGGACTTTA-3'

065979 (anti-sense):
                                    (SEQ ID NO: 28)
5'-TCCAGCCAGCAATACTGCCC-3'
```

Each diagnostic PCR reaction contained a 50 µl total reaction volume with 2 µl of the genomic DNA prepared as described above, 1× ThermoPol buffer (New England Biolabs, Ipswich, Mass., USA), 100 pmol of primer 065978, 100 pmol of primer 065979, 200 µM each of dATP, dCTP, dGTP, and dTTP, and 5 units of Taq DNA polymerase. PCR was performed in an EPPENDORF® MASTERCYCLER® programmed for 1 cycle at 95° C. for 3 minutes followed by 32 cycles each at 95° C. for 30 seconds, 50° C. for 30 seconds, and 72° C. for 2 minutes and 30 seconds. The final extension cycle was at 72° C. for 10 minutes. Following thermocycling, the PCR reaction was separated by 0.9% agarose gel electrophoresis using TAE buffer and the gel photographed under UV light. The presence of a 2379 base pair band indicated appropriate integration of linearized pMhCt036 at the NA1 locus.

The pMhCt036 transformants that tested positive for the 2379 bp band in the diagnostic PCR described above were then confirmed by Southern blot analysis. High quality genomic DNA was prepared from the transformants as well as the control, untransformed strain by the method described above for *A. niger* 803-2 genomic DNA. Genomic DNA was digested with Bgl II or (in a separate reaction) Sac II and Xho I. The digested DNA was separated by 0.9% agarose gel electrophoresis using TAE buffer and then transferred to HYBOND™ N+ membrane using standard techniques as described in Sambrook et al., 1989, *Molecular cloning: A laboratory manual*, Cold Spring Harbor lab., Cold Spring Harbor, N.Y.

An NA1 locus specific Southern probe was prepared using the primers shown below to amplify by PCR an approximately 530 bp region from the *A. niger* NA1 locus.

```
066032 (sense):
                                    (SEQ ID NO: 29)
5'-TGTTCCCTCCOCCCCCTTTTATCTTC-3'

066033 (anti-sense):
                                    (SEQ ID NO: 30)
5'-ATACCGATGTTGGCCCACCACG-3'
```

The PCR reaction (50 µl) was composed of 1× ECONOTAQ® buffer (Lucigen, Middleton, Wis., USA), 50 pmol of primer 066032, 50 pmol of primer 066033, 200 µM each of dATP, dCTP, dGTP, and dTTP, 2.5 units of ECONOTAQ® DNA polymerase (Lucigen, Middleton, Wis., USA), and 100 ng of plasmid pHUda852, The PCR was performed in an EPPENDORF® MASTERCYCLER® programmed for 1 cycle at 95° C. for 3 minutes followed by 30 cycles each at 95° C. for 30 seconds, 55° C. for 30 seconds, and 72° C. for 1 minute. The final extension cycle was at 72° C. for 10 minutes. Following thermocycling, the PCR product was separated by 0.9% agarose gel electrophoresis using TAE buffer and a 538 bp band was excised from the gel and purified using a NUCLEOSPIN® Extract II Kit according to the manufacturer's instructions.

The purified PCR product was digoxigenin-dUTP labeled in an additional PCR reaction, with a 50 µl total reaction volume containing 1× ThermoPol buffer, 50 pmol of primer 066032, 50 pmol of primer 066033, 200 µM each of dATP, dCTP, dGTP, and dTTP, 5 µl of a DIG DNA labeling mixture (Roche Diagnostics, Mannheim, Germany), 20 ng of the original, purified 538 bp NA1 PCR product, and 4 units of Taq DNA polymerase. The PCR conditions were the same as the original reaction. After thermocycling, 5 µl of the PCR reaction were added to 50 µl of TE buffer, heated to 95° C. for 8 minutes, cooled on ice for 10 minutes, and then used as a probe for Southern detection with a DIG High Primer DNA Labeling and Detection Starter Kit II (Roche Diagnostics, Mannheim, Germany) according to the manufacturer's instructions. For the Bgl II digestion, the NA1 locus of *A. niger* M1010 yields a 8460 bp band, while correct integration of pMhCt036 yields a 11,239 bp band. For the Sac II and Xho I digestion, the NA1 locus of *A. niger* M1010 yields a 3552 bp band, while correct integration of pMhCt036 at the NA1 locus yields a 5284 bp band. Three independently isolated transformants, referred to here as cipC036.20, cipC036.24, and cipC036.25, were confirmed to be correct integrants of pMhCt036 at the NA1 locus.

Example 13

Analysis of TcAMG Reporter Activity in Small Scale *A. Niger* Cultures

A COVE-N-Gly plate was streaked with an *A. niger* strain (either the cipC promoter integrants; *A. niger* 01650, a pyrG+ no amyloglucosidase control strain: or *A. niger* 889-852-47, a strain with the triple NA2-tpi-*T. cingulate* amyloglucosidase reporter integrated at the NA1 locus as described above) and allowed to grow for one week at 30° C. A sterile disposable transfer pipet was used to transfer four punched plugs from the plate to a sterile 14-ml polypropylene round bottom tube containing 4 ml of MU1/MLC/urea. Tubes were placed at a slant in a tube rack on an orbital shaker set to 200 rpm and grown at 30° C. for nine days. Tubes were centrifuged at 1942×g for 5 minutes and 200 µl of each supernatant stored at −20° C. for later analysis.

Supernatants from day 9 were assayed for amyloglucosidase activity as follows: Culture supernatants were diluted appropriately in 0.1 M sodium acetate-0.01% TRITON® X-100 pH 5.0 buffer (sample buffer) followed by a series dilution from 0-fold to ⅓-fold to ⅑-fold of the diluted sample. An amyloglucosidase standard (AMG®, Novozymes A/S, Bagsvaerd, Denmark) was diluted using 2-fold steps starting with an 8 AGU/ml concentration and ending with a 1 AGU/ml concentration in the sample buffer. Twenty µl of each dilution including the standard were transferred to a 96-well flat bottom plate. One hundred microliters of a p-nitrophenyl-α-D-glycopyranoside (Sigma Chemical Co., St. Louis, Mo., USA) substrate solution (1 mg/ml in 0.1 M sodium acetate pH 5.0) were added to each well and then incubated at ambient temperature for 45 minutes. Upon completion of the incubation the reaction was quenched with 100 µl of 0.06 N NaOH. The endpoint of the reaction was measured at 405 nm using a BIOMEK® 3000 and BIOMEK® NX Laboratory Automation Workstations (Beckman Coulter, Inc, Fullerton, Calif., USA). Sample concentrations were determined by extrapolation from the generated standard curve.

Each strain was grown in triplicate and the relative average amyloglucosidase activity (relative to *A. niger* 889-85247 as a control strain) and relative standard deviation ("dev.") from the assays are shown below.

| Sample | Relative Avg. AMG Activity | Relative Std. Dev. |
| --- | --- | --- |
| C1650 | 0.00 | 0.00 |
| 889-852-47 | 1.00 | 0.08 |
| cipC036.20 | 0.18 | 0.03 |
| cipC036.24 | 0.20 | 0.04 |
| cipC036.25 | 0.25 | 0.06 |

The results above demonstrated that *A. niger* C1650, a pyrG+ derivative of the *A. niger* M1010 parent strain, did not produce detectable amyloglucosidase activity, but that significant activity from the amyloglucosidase reporter was produced from the cipC promoter in *A. niger* strains cipC036.20, cipC036.24, and cipC036.25. The *A. niger* 889-852-47 positive control strain, with the amyloglucosidase reporter under control of the triple NA2-tpi promoter, produced the highest amyloglucosidase activity in this assay.

Example 14

Fermentation of *Aspergillus Niger* 889-852-47 and *Aspergillus Niger* cipC036.24

*A. niger* cipC036.24 and A, niger 889-852-47 as a control were fermented to evaluate expression of amyloglucosidase under the control of the cipC promoter. Shake flask medium was composed of standard carbon and nitrogen sources. One hundred ml of shake flask medium was added to a 500 ml shake flask for a total of four shake flasks per tank run. Each shake flask was inoculated with a volume of liquid spore suspension corresponding to a total spore count of 1 to 2 million spores and incubated at 30° C. on an orbital shaker at 220 rpm for 72 hours. Fifty ml from each of four shake flask broths was used to inoculate a 2 liter fermentation vessel. Fermentation batch medium was composed of standard carbon and nitrogen sources at pH 5.

A total of 1.8 liters of the fermentation batch medium was added to an Applikon Biotechnology two liter glass jacketed fermentor (Applikon Biotechnology Inc., Foster City, Calif., USA). The fermentation vessel was maintained at a temperature of 34° C. and the pH was controlled using an Applikon 1030 control system (Applikon Biotechnology Inc., Foster City, Calif., USA) to a set-point of 4.85+/−0.1. Sterile air was added to the vessel at a rate of 1 vvm and the broth was agitated by a Rushton impeller rotating at 1100 rpm. The fermentation ran for 185 hours.

Figure 3:
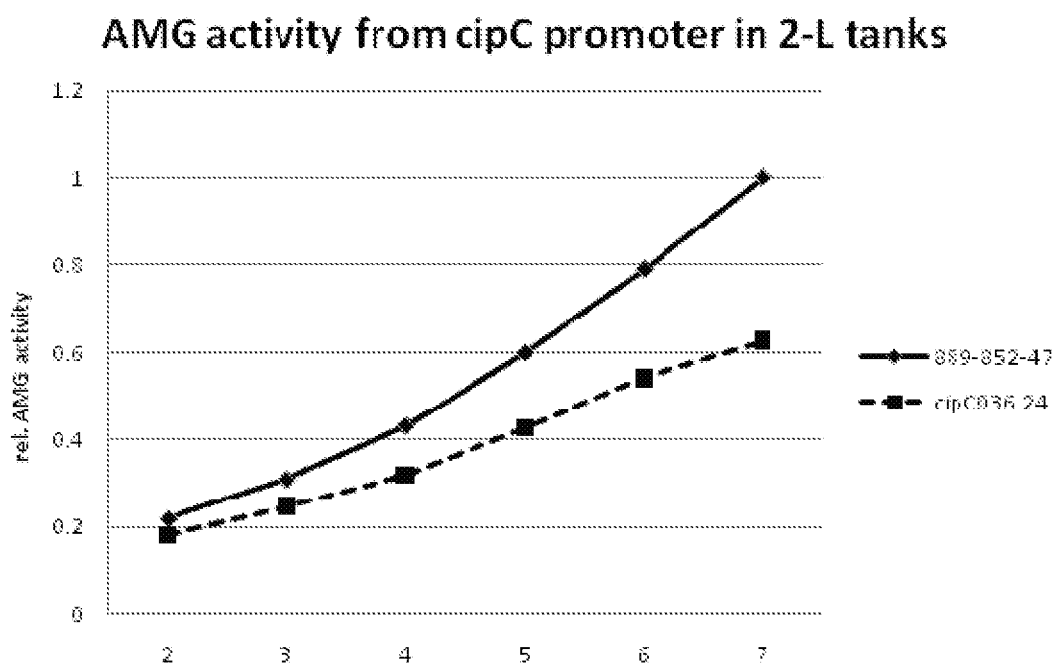
FIG. 3 shows relative amyloglucosidase yields from fermentation of *Aspergillus niger* 889-852-47 and *Aspergillus niger* cipC036.24.

Samples were taken daily from the fermentation tanks and assayed for amyloglucosidase activity according to the assay described in Example 13. The results are shown in FIG. 3. Significant activity from the amyloglucosidase reporter was produced from the cipC promoter in *A. niger* strain cipC036.24.

The present invention is further described by the following numbered paragraphs:

[1] A method for producing a polypeptide, comprising: (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence having at least 60% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32, (ii) a promoter comprising a nucleotide sequence that hybridizes under at least medium stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof; (iii) a promoter comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (iv) a promoter comprising a subsequence of (i), (ii), or (iii) that retains promoter activity; and (v) a mutant, hybrid, or tandem promoter of (i), (ii), (iii), or (iv): wherein the polynucleotide encoding the polypeptide is foreign to the promoter; and (b) isolating the polypeptide from the cultivation medium.

[2] The method of paragraph 1, wherein the promoter comprises a nucleotide sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32.

[3] The method of paragraph 1, wherein the promoter comprises a nucleotide sequence that hybridizes under medium stringency conditions, medium-high stringency conditions, high stringency conditions, or very high stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof.

[4] The method of paragraph 1, wherein the promoter comprises or consists of the polynucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or a subsequence thereof that has promoter activity.

[5] The method of paragraph 4, wherein the promoter comprises or consists of the polynucleotide sequence of SEQ ID NO: 1, SEQ ID NO: 2, SEQ ID NO: 3, SEQ ID NO: 4, SEQ ID NO: 5 SEQ ID NO: 6, SEQ ID NO: 7 SEQ ID NO: 8, SEQ ID NO: 31, or SEQ ID NO: 32.

[6] The method of paragraph 1, wherein the promoter is a hybrid promoter comprising one or more (e.g., several) portions of the polynucleotide sequences of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

[7] The method of paragraph 1, wherein the promoter is a tandem promoter comprising one or more (e.g., several) polynucleotide sequences of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; or a subsequence thereof that retains promoter activity.

[8] The method of paragraph 7, wherein the promoter is a tandem promoter comprising one or more (e.g., several) polynucleotide sequences of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

[9] The method of paragraph 7 or 8, wherein the tandem promoter comprises two or more (e.g., several) promoters.

[10] The method of paragraph 9, wherein the two or more (e.g., several) promoters of the tandem promoter simultaneously promote the transcription of the polynucleotide.

[11] The method of paragraph 10, wherein one or more (e.g., several) of the two or more (e.g., several) promoters of the tandem promoter promote the transcription of the polynucleotide encoding the polypeptide at different stages of growth of the fungal host cell.

[12] The method of any of paragraphs 1-11, wherein the fungal host cell contains one or more (e.g., several) copies of the polynucleotide encoding the polypeptide.

[13] The method of any of paragraphs 1-11, wherein the fungal host cell contains one copy of the polynucleotide encoding the polypeptide.

[14] The method of any of paragraphs 1-13, wherein the polypeptide is selected from the group consisting of an antigen, enzyme, growth factor, hormone, immunodilator, neurotransmitter, receptor, reporter protein, structural protein, and transcription factor.

[15] The method of any of paragraphs 1-14, wherein the polypeptide is native or foreign to the fungal host cell.

[16] The method of any of paragraphs 1-15, wherein the polynucleotide is contained in the chromosome of the fungal host cell.

[17] The method of paragraph 1, wherein the polynucleotide is contained on an extrachromosomal element.

[18] The method of any of paragraphs 1-17, wherein the fungal host cell is a filamentous fungal cell.

[19] The method of any of paragraphs 1-17, wherein the fungal host cell is a yeast cell.

[20] An isolated promoter selected from the group consisting of (1) a promoter comprising a nucleotide sequence having at least 60% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (ii) a promoter comprising a nucleotide sequence that hybridizes under at least medium stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof; (iii) a promoter comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; (iv) a promoter comprising a subsequence of (i), (ii), or (iii) that retains promoter activity; and (v) a mutant, hybrid, or tandem promoter of (i), (ii), (iii), or (iv).

[21] The promoter of paragraph 20, which comprises a nucleotide sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32.

[22] The promoter of paragraph 20, which comprises a nucleotide sequence that hybridizes under medium stringency conditions, medium-high stringency conditions, high stringency conditions, or very high stringency conditions with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or the full-length complement thereof.

[23] The promoter of paragraph 20, which comprises or consists of the polynucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32; or a subsequence thereof that has promoter activity.

[24] The promoter of paragraph 23, which comprises or consists of the polynucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, or SEQ ID NO: 32.

[25] The promoter of paragraph 20, which is a hybrid promoter comprising one or more (e.g., several) portions of the polynucleotide sequences of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

[26] The promoter of paragraph 20, which is a tandem promoter comprising one or more (e.g., several) polynucleotide sequences of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; or a subsequence thereof that retains promoter activity.

[27] The promoter of paragraph 26, which is a tandem promoter comprising one or more (e.g., several) polynucleotide sequences of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

[28] The promoter of paragraph 26 or 27, wherein the tandem promoter comprises two or more (e.g., several) promoters.

[29] The promoter of paragraph 28, wherein the two or more (e.g., several) promoters of the tandem promoter simultaneously promote the transcription of a polynucleotide encoding a polypeptide.

[30] The promoter of paragraph 28, wherein one or more (e.g., several) of the two or more (e.g., several) promoters of the tandem promoter promote the transcription of a polynucleotide encoding a polypeptide at different stages of growth of the fungal host cell.

[31] A nucleic acid construct comprising a polynucleotide encoding a polypeptide operably linked to the promoter of any of paragraphs 20-30.

[32] A recombinant expression vector comprising the nucleic acid construct of paragraph 31.

[33] A recombinant host cell comprising the nucleic acid construct of paragraph 31.

[34] The recombinant host cell of paragraph 33, which is a filamentous fungal cell.

[35] The recombinant host cell of paragraph 33, which is a yeast cell.

[36] A nucleic acid construct comprising (a) a targeting sequence, (b) the promoter of any of paragraphs 20-30, (c) an exon, and (d) a splice-donor site.

[37] A nucleic acid construct comprising (a) a targeting sequence, (b) a promoter of any of paragraphs 20-30, (c) an exon, (d) a splice-donor site, (e) an intron, and (f) a splice-acceptor site, wherein the targeting sequence directs the integration of elements (a)-(f) such that elements (b)-(f) are operably linked to an endogenous gene.

[38] A method for producing a polypeptide comprising (a) cultivating a homologously recombinant cell, having incorporated therein a transcription unit comprising a promoter of any of paragraphs 20-30, an axon, and/or a splice donor site operably linked to a second exon of an endogenous polynucleotide encoding the polypeptide, under conditions conducive for production of the polypeptide, wherein the polynucleotide encoding the polypeptide is foreign to the promoter: and (b) recovering the polypeptide The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide, comprising:
   (a) cultivating a fungal host cell in a medium conducive for the production of the polypeptide, wherein the fungal host cell comprises a polynucleotide encoding the polypeptide operably linked to a promoter selected from the group consisting of (i) a promoter comprising SEQ ID NO: 1 or a subsequence thereof that retains promoter activity, (ii) a promoter comprising a nucleotide sequence that hybridizes under at least high stringency conditions with SEQ ID NO: 1 or the full-length complement thereof, wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.; and (iii) a hybrid or tandem promoter of (i) or (ii); wherein the polynucleotide encoding the polypeptide is foreign to the promoter; and
   (b) isolating the polypeptide from the cultivation medium.

2. The method of claim 1, wherein the promoter comprises a nucleotide sequence that hybridizes under high stringency conditions with SEQ ID NO: 1 or the full-length complement thereof, wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.

3. The method of claim 1, wherein the promoter comprises a nucleotide sequence that hybridizes under very high stringency conditions with SEQ ID NO: 1 or the full-length complement thereof, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

4. The method of claim 1, wherein the promoter comprises the polynucleotide sequence of SEQ ID NO: 1; or a subsequence thereof that retains promoter activity.

5. The method of claim 1, wherein the promoter is a hybrid promoter comprising a portion of SEQ ID NO: 1 and one or more portions of the polynucleotide sequences of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, and SEQ ID NO: 32.

6. The method of claim 1, wherein the promoter is a tandem promoter comprising SEQ ID NO: 1 and one or more polynucleotide sequences of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, and SEQ ID NO: 32; or a subsequence(s) thereof that retains promoter activity.

7. The method of claim 1, wherein the polypeptide is native or foreign to the fungal host cell.

8. The method of claim 1, wherein the fungal host cell is a filamentous fungal cell.

9. The method of claim 1, wherein the fungal host cell is a yeast cell.

10. A nucleic acid construct comprising a polynucleotide encoding a polypeptide operably linked to a promoter, wherein the polynucleotide encoding the polypeptide is foreign to the promoter and wherein the promoter is selected from the group consisting of (i) a promoter comprising SEQ ID NO: 1 or a subsequence thereof that retains promoter activity, (ii) a promoter comprising a nucleotide sequence that hybridizes under at least high stringency conditions with SEQ ID NO: 1 or the full-length complement thereof, wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.; and (iii) a hybrid or tandem promoter of (i) or (ii).

11. The nucleic acid construct of claim 10, which comprises a nucleotide sequence that hybridizes under high stringency conditions with SEQ ID NO: 1; or the full-length complement thereof, wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.

12. The nucleic acid construct of claim 10, which comprises the polynucleotide sequence of SEQ ID NO: 1 or a subsequence thereof that retains promoter activity.

13. The nucleic acid construct of claim 10, which is a hybrid promoter comprising a portion of SEQ ID NO: 1 and one or more portions of the polynucleotide sequences of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, and SEQ ID NO: 32.

14. The nucleic acid construct of claim 10, which is a tandem promoter comprising SEQ ID NO: 1 and one or more polynucleotide sequences of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, and SEQ ID NO: 32; or a subsequence(s) thereof that retains promoter activity.

15. A recombinant host cell comprising the nucleic acid construct of claim 10.

16. The recombinant host cell of claim 15, which is a filamentous fungal cell.

17. The recombinant host cell of claim 15, which is a yeast cell.

18. The nucleic acid construct of claim 10, which comprises a nucleotide sequence that hybridizes under very high stringency conditions with SEQ ID NO: 1 or the full-length complement thereof, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

19. The method of claim 1, wherein the promoter consists of the polynucleotide sequence of SEQ ID NO: 1 or a subsequence thereof that retains promoter activity.

20. The nucleic acid construct of claim 10, which consists of the polynucleotide sequence of SEQ ID NO: 1 or a subsequence thereof that retains promoter activity.

* * * * *

SEQUENCE LISTING

<160> NUMBER OF SEQ ID NOS: 32

<210> SEQ ID NO 1
<211> LENGTH: 1002
<212> TYPE: DNA
<213> ORGANISM: Aspergillus niger

<400> SEQUENCE: 1

```
caagacgaga agctgaccgg gtcgaccggc tcatctcacg cccgccaaga ctgggcaaac      60
tgtggctgcg gcgctaaatg gaccagaatg gattcgccca gacttaaggc tgaggagatc     120
cccatctcga cccagtcgcc cagcaataac atcgtggttc cgaccctgga cgcgtacgta     180
cgcactctgc tcaggcgatg atccggatgg tcgttgctcc aggccgtgag gactccaact     240
ggcctgcagg agacacacgc aagggcatct gcatggcccc caaaacgaag agcaggaaca     300
gtcactagat agatagtagc ctatcaccgt tgtagcctat gcgcggtgta gacagtcgct     360
gcctcggccg taagaattga ctaagagggg cacacgattg atgctcccaa agtgaccacg     420
gatccccaac cggagataca tgattcctct tacatgattg aacccgatg  tttcaactttt    480
ttgaggctag tagcttaccc ctcgactgcc ctcctggac  aattccgtgc ccatcacatc     540
gctccacgag gctgtggctt ggtgcttctc gccctcactg ccgctcaatt attcggtttc     600
tcgtagcgtc taagcgacgg tttgttccaa tcaaatcccg atccatctat tctccccaag     660
cgctgcctcc tttgcgcagt ttcagctggc ctgtgtccac tcccttcact ggatgtgatc     720
ttttcctcga tccacccttt cacagtcggg agcgaaccat attgttcttt atccgacgcc     780
ccaagacttt cgatgcattt ccgtgagatt agacggtggg gcactctgag gatgggcgat     840
ggaggggcgc cccaagagag ctgaagatgc tgagtagggt tgtccaggca gcacatatat     900
aagatgctct gtcccctccc atcgagtcct tcttttctct ctctcatcaa tcactctact     960
tcctactcta ccttaaactc ttcactactt catacatcaa tc                       1002
```

<210> SEQ ID NO 2
<211> LENGTH: 1005
<212> TYPE: DNA
<213> ORGANISM: Aspergillus niger

<400> SEQUENCE: 2

```
caagacgaga agctgaccgg gtcgaccggc tcatctcacg cccgccaaga ctgggcaaac      60
tgtggctgcg gcgctaaatg gaccagaatg gattcgccca gacttaaggc tgaggagatc     120
cccatctcga cccagtcgcc cagcaataac atcgtggttc cgaccctgga cgcgtacgta     180
cgcactctgc tcaggcgatg atccggatgg tcgttgctcc aggccgtgag gactccaact     240
ggcctgcagg agacacacgc aagggcatct gcatggcccc caaaacgaag agcaggaaca     300
gtcactagat agatagtagc ctatcaccgt tgtagcctat gcgcggtgta gacagtcgct     360
gcctcggccg taagaattga gactaagagg ggcacacgat tgatgctccc aaagtgacca     420
cggatcccca accggagata catgattcct cttacatgat tggaacccga tgtttcaact     480
tttttgaggct agtagcttac ccctcgactg ccctcctgg acaattccgt gcccatcaca     540
tcgctccacg aggctgtggc ttggtgcttc tcgccctcac tgccgctcaa ttattcggtt     600
tctcgtagcg tctaagcgac ggtttgttcc aatcaaatcc cgatccatct attctcccca     660
agcgctgcct cctttgcgca gtttcagctg gcctgtgtcc actcccttca ctggatgtga     720
tcttcccctc gatccacccT ttcacagtcg ggagcgaacc atattgttct ttatccgacg     780
ccccaagac  tttcgatgca tttccgtgag attagacggt ggggcactct gaggatgggc     840
```

```
gatggagggg cgccccaaga gagctgaaga tgctgagtag ggttgtccag gcagcacata    900
tataagatgc tctgtcccct cccatcgagt ccttctttcc tctctctcat caatcactct    960
acttcctact ctaccttaaa ctcttcacta cttcatacat caatc                   1005
```

<210> SEQ ID NO 3
<211> LENGTH: 1005
<212> TYPE: DNA
<213> ORGANISM: Aspergillus niger

<400> SEQUENCE: 3

```
caagacgaga agctgaccgg gtcgaccggc tcatctcacg cccgccaaga ctgggcaaac     60
tgtggctgcg gcgctaaatg gaccagaatg gattcgccca gacttaaggc tgaggagatc    120
cccatctcga cccagtcgcc cagcaataac atcgtggttc cgaccctgga cgcgtacgta    180
cgcactctgc tcaggcgatg atccggatgg tcgttgctcc aggccgtgag gactccaact    240
ggcctgcagg agacacacgc aagggcatct gcatggcccc caaaacgaag agcaggaaca    300
gtgactagat agatagtagc ctatcaccgt tgtagcctat gctcggtgta gacagtcgct    360
gcctcggccg taagaattgg actaagaggg gcacacgatt gatgctccca aagtgaccac    420
ggatccccaa ccggagatac atgattcctc ttacatgatt ggaacccgat gtttcaactt    480
tttgaggcta gtagcttacc cctcgactgc ccctcctgga caattccgtg cccatcacat    540
cgctccacga ggctgtggct tggtgcttct cgccctcact gccgctcaat tattcggttt    600
ctcgtagcgt ctaagcgacg gtctgttcca atcaaatccc gatccatcta ttctccccaa    660
gcgctgcctc ctttgcgcag tttcagctgg cctgtgtcca ctcccttcac tggatgtgat    720
cttctcctcg atccacccct tcacagtcgg gagcgaacca tattgttctt tatccgacgc    780
cccaagactc tttcgatgca tttcggtgag attagacggt ggggcactct gaggatgggc    840
gatggagggg cgccccaaga gagctgaaga tgctgagtag ggttgtccag gcagcacata    900
tataagatgc ttcgtcccct cccatcgagt ccttctttc  tctctctcat caatcactct    960
acttcctact ctaccttaaa ctcttcacta cttcatacat caatc                   1005
```

<210> SEQ ID NO 4
<211> LENGTH: 1005
<212> TYPE: DNA
<213> ORGANISM: Aspergillus niger

<400> SEQUENCE: 4

```
caagacgaga agctgaccgg gtcgaccggc tcatctcacg cccgccaaga ctgggcaaac     60
tgtggctgcg gcgctaaatg gaccagaatg gattcgccca gacttaaggc tgaggagatc    120
cccatctcga cccagtcgcc cagcaataac atcgtggttc cgaccctgga cgcgtacgta    180
cgcactctgc tcaggcgatg atccggatgg tcgttgctcc aggccgtgag gactccaact    240
ggcctgcagg agacacacgc aagggcatct gcatggcccc caaaacgaag agcaggaaca    300
gtcactagat agatagtagc ctatcaccgt tgtagcctat gcgcggtgta gacagtcgct    360
gcctcggccg taagaattga gactaagagg ggcacacgat tgatgctccc aaagtgacca    420
cggatcccca accggagata catgattcct cttacatgat tggaacccga tgtttcaact    480
ttttgaggct agtagcttac ccctcgactg cccctcctgg acaattccgt gcccatcaca    540
tcgctccacg aggctgtggc ttggtgcttc cgccctcac tgccgctcaa ttattcggtt    600
tctcgtagcg tctaagcgac ggtttgttcc aatcaaatcc cgatccatct attctcccca    660
```

```
agcgctgcct cctttgcgca gtttcagctg gcctgtgtcc actcccttca ctggatgtga    720
tcttcccctc gatccaccct ttcacagtcg ggagcgaacc atattgttct ttatccgacg    780
cccccaagac tttcgatgca tttccgtgag attagacggt ggggcactct gaggatgggc    840
gatggagggg cgcccaaga gagctgaaga tgctgagtag ggttgtccag gcagcacata    900
tataagatgc tctgtcccct cccatcgagt ccttcttttc tctctctcat caatcactct    960
acttcctact ctaccttaaa ctcttcacta cttcatacat caatc                   1005
```

<210> SEQ ID NO 5
<211> LENGTH: 1000
<212> TYPE: DNA
<213> ORGANISM: Aspergillus terreus

<400> SEQUENCE: 5

```
cacttccatt gcgatgtgct cgcagatccg tagggcgtag ggcagagaga caagccttgg     60
acaagagaag cttggcgagc gttggcctcg gttgcgccgg ccctatcgtg ctagtaccac    120
gacccgcact gagtggctga gtcgtgctca accagtaagg ctgagtccca ggcccatcca    180
cttactagta actattatta tggagggttt acggagtacg gagtattagc ggcccagccg    240
atcagcagga gcttcggacg gtcgacacgt atgttgtccg ccgatcctca ccgtctgttt    300
tggacatccc atgcggtact cagtacaggt acatactccg tacttcgtag atatcggaag    360
gcatccgctg cagtggggag ttgggagtgt agggagtacg gaatctcttc ggtaggatgc    420
tcgggattat cgggctgcat tgcgtcttca tgcacggtct cccatgtatc atcctcagct    480
caagccactc ccagccaatt gccgctgggc cgtggctgaa cgcgtacgcc gcgccagatt    540
atgacccctc aagctaacgc tccttcagcc gtggctgagt gggagaccgg ctcgcggtgg    600
agggtcccgg tgatcatccc atgcgcgtgt ttcacacgat gccctctacg gtcaatgtgg    660
cggtaagtcc tcctcagcca cgggatgaca tggccaatcg atccatctcg gccggtggag    720
gacgatgctg accgccagag accagggccc ggcgattcca cgagatgaga cggtggggca    780
gatggtgtgt ggtagatgga ggggtaggag acgctgaggg taggagtaga ccgaggggtt    840
gtccgagggg tcgtccgagg ggtagtgctg gaagggttat aataaggtcg tcctctcctc    900
tgaattgagc atcttcatct tcatctcatc ttcactcaac acatcttcac cactctctca    960
tctttctctt tcttacctct tctcatcaca tatcttcaca                        1000
```

<210> SEQ ID NO 6
<211> LENGTH: 1000
<212> TYPE: DNA
<213> ORGANISM: Aspergillus oryzae

<400> SEQUENCE: 6

```
gccgttcttc cttattgtcc aggtgctgtt gctcgcgcga tttatagcca ggtctcagcc     60
aacaccaggt cttcttcgat ttgtttgatt gatattgtac aagcaatcaa aaaaaatatt    120
caaagcttgg ttcaaagcaa tagaacaaag ttcgcaggaa gaccgagcag aacatccata    180
gagctgcgcc tgatgccaag gtgcatatca cggtaaatga taaatgtatg aaggaaatgt    240
ggtcctattc ctttgaacta tctaagggtt atgtctgctt aaataccca tccagaactt    300 cttgttcaat gtttgttgtt cctgtttctt tgccgctaga tcatgcggca tgccactgtg    360
gatatatgtc acaagtagta ttctttttcta tatataattc tagtaaaaac tatactcgtt    420
gcaagcacct tgatgactta taatgtattg atcgaggcta actaactaag aaaaactgac    480
tgcatagtaa attattaagt ataaaataaa cataaacaaa ctgtaaaccg gtaaccagaa    540
```

```
taatatgatc aaaaaatgga tggtttcaaa cttttgacat cccactgtag ggccgccaga    600
tggaatgccc taccaaccaa cataaatacg tacctctcct ccacctcgct accgcgtact    660
gtgaagggat ctcttcgcct atttccgatc taagcattag tgtggggcaa tttgtgggcc    720
aggcgacaga tctatccact tcacggttgc aaaataagga tatgattgga cctgatgggg    780
ggcatcttga ctagctgaag gagcagggg gagctgaaca tgggattttc gggtcacaac     840
acagcatggt ggagtggggt ttgtgggctg ccagctcgca gcattataag atactcctcg    900
tctccctcgt tttcatcctt tttttttctt tattaaacac tattcttcat gatattttat    960
ttactacttt cctatcccgt ccatactctc atctgcaaaa                         1000

<210> SEQ ID NO 7
<211> LENGTH: 1000
<212> TYPE: DNA
<213> ORGANISM: Aspergillus fumigatus

<400> SEQUENCE: 7
gcaaatcgat gctagcaatc actagctgag tcgatcaggc gaatcattcg attctgaagt     60
gctaattaca gtagtgtgga ttttatggct catctgaagt acggctgagc gaaagaccca    120
tataccagtt gatccacggt cgaatggatg actctgatcc attactacat gggcagtgaa    180
gaactcacta ccggccgaaa agtcataata acagcagtgg catggaatag tctcgacttg    240
tattaacatc ctcaaggctg caatatttta gcgctggtct aacgccttct aagctcctat    300
agttggggac tggtgccatg ggagagagag ggggtgggac ggtgattctt cctccgagtt    360
cagatccgag accatcttgc tcgtaataat acagtcacga cagcgaata ctactgctta     420 aaatctgagg caattcttct agctgaaaact actccgtcgt ccttgtggag caatcgcttc    480
actagctgga gtacggggtc ccctccaact tcgtgtcgca cgccgcagct ggcaagtctc    540
caaaagtgga cagacgctgt ggcgcttgcg accactattc acgtaatccg aaagatcgtg    600
ggacggtagc agcgggaatc ggtcctctgg agttagtagt acatgaccac ttgggagaaa    660
ggtgcggcca ttccattccc gtcatcgtac tacgtattat cctttacacc cctctcaagg    720 aaagggggcgc aagatgaccc gtccgatctc cttgaccaac tcataaggc ttagcagtgg     780 agctgtggac ggtaggtgct gagacgataa cctgagaggg gcaatgaggc cttttgagtt    840
ccctgagata gctgataacc ccgccctgtg cagggatata agttgagcag actgcctccc    900
cctctgtgat cccgagctat cccattgtta actatcacaa caccttcaa ctgcctttag     960 aatcttaaat tctttcttga tttcaccaga tcaactcaaa                         1000

<210> SEQ ID NO 8
<211> LENGTH: 1000
<212> TYPE: DNA
<213> ORGANISM: Aspergillus nidulans

<400> SEQUENCE: 8
tcaatgtcac atcttccctg ttaaggtaga tccttaacaa actatttcgt tatctacagg     60
agagtcatat tgtacacaca tctcggtgca atggaggtat ccggtgaatt gaaatgctgg    120
aaatgctgga aatgctgcaa gtttgggatc ccacagacca gaaactctcc atggtcctaa    180
aaacacctga aatatatatg aatgtggccc aacaacagca acagggtcat gacaaggtct    240
gtccaaaagc ggcgactgaa cccgtggtt ccgctgatat atctcccgga gaagggttcc     300
tacatcgact gctcatctgg cgttccattg accgtttgcc agaggctccc gattgcatta    360
```

```
tcagggccta gctgaccccc taacaagata acgaagtcc ctcgggtcac gtgggcctga    420
aacgagtctc tgctccaagt ataagtagta ataccctcact caaatttagc ctgaaccgtt   480
acttgtgcca tcgtccgccc acccacgtcg ccgtatgctg agcggtgtgc ctactatgga   540
tcatttatac ggtgagtcac tatagaaccg cagataaagc tgctgcctgg agctccagtc   600
ggagcgatcg gatcgaatta ttctcaatgg gcatgggaga acggggcgat caacaaagct   660
aagccctctg agggaattct tagccttct tggcccttcc attggccaat cacagccggt    720
ttgtggctgg gtccagcaaa gcttagggac aatagtgttt cgggctatta ttatcgcaat   780
tctccgtgta cctcagccag tcccacgatg ctgctgtggc tgggcacctg ctcagctcgt   840
atagaatact tgtaaggcgt aggggaagac attctacccc gcttctgagg ggtataaaga   900
gacctacccc tgaccccttc tttctttgct caatcctcca agaatattca tattactcta   960
ccgcactcgt tctcttcctt attatatcac atcaagcatt                         1000
```

<210> SEQ ID NO 9
<211> LENGTH: 30
<212> TYPE: DNA
<213> ORGANISM: Trametes cingulata

<400> SEQUENCE: 9

```
tgggggatcc accatgcgtt tcacgctcct                                      30
```

<210> SEQ ID NO 10
<211> LENGTH: 33
<212> TYPE: DNA
<213> ORGANISM: Trametes cingulata

<400> SEQUENCE: 10

```
ctcgagttaa ttaactaccg ccaggtgtcg ttc                                  33
```

<210> SEQ ID NO 11
<211> LENGTH: 36
<212> TYPE: DNA
<213> ORGANISM: Aspergillus nidulans

<400> SEQUENCE: 11

```
tttgctagca ctagttacta aatgacgttt gtgaac                               36
```

<210> SEQ ID NO 12
<211> LENGTH: 40
<212> TYPE: DNA
<213> ORGANISM: Aspergillus nidulans

<400> SEQUENCE: 12

```
ctaccgccag gtgtcagtca ccctcaaagt ccaactcttt                           40
```

<210> SEQ ID NO 13
<211> LENGTH: 40
<212> TYPE: DNA
<213> ORGANISM: Aspergillus niger

<400> SEQUENCE: 13

```
aaagagttgg actttgaggg tgactgacac ctggcggtag                           40
```

<210> SEQ ID NO 14
<211> LENGTH: 30
<212> TYPE: DNA
<213> ORGANISM: Aspergillus niger

<400> SEQUENCE: 14

```
tctctagagg agagagttga acctggacgc                                              30

<210> SEQ ID NO 15
<211> LENGTH: 29
<212> TYPE: DNA
<213> ORGANISM: Aspergillus niger

<400> SEQUENCE: 15
ggcggccgcg tttaaaccta tctgttccc                                               29

<210> SEQ ID NO 16
<211> LENGTH: 37
<212> TYPE: DNA
<213> ORGANISM: Aspergillus niger

<400> SEQUENCE: 16
tcgtctagag ctagctgact tctatataaa aatgagt                                      37

<210> SEQ ID NO 17
<211> LENGTH: 24
<212> TYPE: DNA
<213> ORGANISM: Aspergillus niger

<400> SEQUENCE: 17
tcctctagag tatatgatgg tact                                                    24

<210> SEQ ID NO 18
<211> LENGTH: 34
<212> TYPE: DNA
<213> ORGANISM: Aspergillus niger

<400> SEQUENCE: 18
ggagaattct taattaagca ttctcctagt tact                                         34

<210> SEQ ID NO 19
<211> LENGTH: 39
<212> TYPE: DNA
<213> ORGANISM: Trametes cingulata

<400> SEQUENCE: 19
ttatatagaa gtcagctagc caagacgaga agctgaccg                                    39

<210> SEQ ID NO 20
<211> LENGTH: 45
<212> TYPE: DNA
<213> ORGANISM: Trametes cingulata

<400> SEQUENCE: 20
aaacgcatgg tggatccccc gattgatgta tgaagtagtg aagag                             45

<210> SEQ ID NO 21
<211> LENGTH: 45
<212> TYPE: DNA
<213> ORGANISM: Trametes cingulata

<400> SEQUENCE: 21
ctcttcacta cttcatacat caatcggggg atccaccatg cgttt                             45

<210> SEQ ID NO 22
<211> LENGTH: 18
<212> TYPE: DNA
<213> ORGANISM: Trametes cingulata
```

<400> SEQUENCE: 22
aacttgggct cgccgagg                                                      18

<210> SEQ ID NO 23
<211> LENGTH: 20
<212> TYPE: DNA
<213> ORGANISM: Aspergillus niger

<400> SEQUENCE: 23
aatccggatc ctttcctata                                                    20

<210> SEQ ID NO 24
<211> LENGTH: 20
<212> TYPE: DNA
<213> ORGANISM: Aspergillus niger

<400> SEQUENCE: 24
gatggagcgc gcctagaagc                                                    20

<210> SEQ ID NO 25
<211> LENGTH: 20
<212> TYPE: DNA
<213> ORGANISM: Trametes cingulata

<400> SEQUENCE: 25
tgattgcaag tccgagcaca                                                    20

<210> SEQ ID NO 26
<211> LENGTH: 20
<212> TYPE: DNA
<213> ORGANISM: Trametes cingulata

<400> SEQUENCE: 26
gaggtttgtc cgatgcgatt                                                    20

<210> SEQ ID NO 27
<211> LENGTH: 22
<212> TYPE: DNA
<213> ORGANISM: Aspergillus nidulans

<400> SEQUENCE: 27
gttgggcgag gtgcggactt ta                                                 22

<210> SEQ ID NO 28
<211> LENGTH: 20
<212> TYPE: DNA
<213> ORGANISM: Aspergillus niger

<400> SEQUENCE: 28
tccagccagc aatactgccc                                                    20

<210> SEQ ID NO 29
<211> LENGTH: 26
<212> TYPE: DNA
<213> ORGANISM: Aspergillus niger

<400> SEQUENCE: 29
tgttccctcc cccccttttt atcttc                                             26

<210> SEQ ID NO 30
<211> LENGTH: 22
<212> TYPE: DNA
<213> ORGANISM: Aspergillus niger

<400> SEQUENCE: 30

```
ataccgatgt tggcccacca cg                                              22
```

<210> SEQ ID NO 31
<211> LENGTH: 1000
<212> TYPE: DNA
<213> ORGANISM: Trichoderma reesei

<400> SEQUENCE: 31

```
ctgcccagtg catgttcctc gtccttcggg gtcccttcat tgacaaggat cccgcggaac     60
aggatggtgg gggaggcgca atggcggggt gctcgggaaa agcctccaaa aagcttgacc    120
agccatagct ccgacccagc caggatgcca gtctagcatc attgaatcga tagccattcg    180
tatgtgtgcc cgcctctgct cgtatgtatg cacctgaagt catgccacat tcagctgctc    240
agggattaca gcataaatca agccagggca gacacccccc ttgtgtcaat ggccctcgtc    300
ggagaatctg tagagtgaga atgatgcgc ctctggccc cccctccaac tccgtccttc    360
ccatgcgcca ctttgagagg atatgacgtt cgcaatgctc aaaatcaggg ggaacaagga    420
cgggtggcct cacggcctgt gagccatggc ctgggccaca aagtgccga gcttctccac    480
gattaggggg tgcttgccat gcaactgtgt ccagccgggc ctgcttgcca gcatccagct    540
gctctcttgc gtggggaccc ttggaccccg tttgccacac tacgtatgtg ctgagagcca    600
ccaatcgcgt tatcatagta gctctggagc tgttgcgagt ccggatcatc aagatgtgcg    660
caggctggag ggcgtcagcg tgtccacgca tgaagctcgc ccacgcccct ttctccacgc    720
tgctacgcca tcgaaacttg ccagaatagc aacgcagtag cttcggggc gtacgagtag    780
ctgtatgtat gtatgcgtgg ccaaggggca ggtggctgtt tcgtagatca ccgggtgtcc    840
tgagagggtg aggcctctaa cccctcttga ggagcgtggc agcttgaagc ttataaatag    900
ccctttgttc tccctcagaa accttcctct tcttctcccc ttcaagcaaa cactcctcac    960
acaaaccaca cacaacactc aacttctctt catattcaca                         1000
```

<210> SEQ ID NO 32
<211> LENGTH: 1000
<212> TYPE: DNA
<213> ORGANISM: Trichoderma reesei

<400> SEQUENCE: 32

```
cgacacgatc tcctggccta tggcgtaggg cgccgtcaag ccttggacaa gagaagctta     60
gcggggtcg accggcttcg gaatttgtgg ctcccgtggc tgatgaccgt atttttagtt    120
tacgcgccca ggagtaaggc tgaggggca cgacccagtc agtgccaagt ggatccattc    180
gatcggcgct gcatagccta tggatctctg gagacacgta tgtccctaga ctcactacgg    240
tgtcccgctc atgagaagac gaatggtttc gccctgacgc tcttccaacg ataacagtat    300
cttctatcat ccatctactg tgtactatgt agccgtcctt caatctccga tgcctaaggc    360
aggattctat tgaacgagca taacgcgctc ggtgctacga ggaatgagga ccttgatcca    420
ctccaatctt tgttacgttt caagccacgc ccctctcctc tgccaagagc cccgacaact    480
ggatcatgtc catcgaaccc ataccgtggt tggattcaac aaaaaccatag tctggtaccg    540
gaggaagcta agcgccagcg tctcctcgtc tcggtggctt ggcggtggct gatgtgcatc    600
ttcgcgcatc gaagcactcc tatcagtgat cgcctcctat gccgcacccg ctgttatgct    660
tttggtaacg tggcagtctc tgcgtctgat cactggatgt gatctgttcg attggtccac    720
```

```
cacccatcgc atgggttgcc tcccttctcg cctaggtccg aaatccgatc ctcatgagat    780
gagataggtg gggcagagag caacgtaggc agatggaggg gtagcgataa gctgaagagt    840
acgccagctt ggtgggggtg tcggggtata ttaagacgta tcgcacccac tgctgctcag    900
actattcttc tcatcattct ctgcaaaata tcctgttcct ctcatccata tccatcttct    960 cccctttttat tttctttaca taccgcataa atcattcaca                        1000
```